United States Patent
Baertschi et al.

(10) Patent No.: US 8,089,227 B2
(45) Date of Patent: Jan. 3, 2012

(54) ELECTRICALLY OPERATED, CONTINUOUSLY ADJUSTABLE PERSONAL HYGIENE DEVICE

(75) Inventors: Armin Baertschi, Winznau (CH); Franz Fischer, Triengen (CH); Christian Hilfiker, Triengen (CH)

(73) Assignee: Trisa Holding AG, Triengen (CH)

( * ) Notice: Subject to any disclaimer, the term of this patent is extended or adjusted under 35 U.S.C. 154(b) by 548 days.

(21) Appl. No.: 12/223,748

(22) PCT Filed: Mar. 14, 2007

(86) PCT No.: PCT/EP2007/002241
§ 371 (c)(1),
(2), (4) Date: Aug. 27, 2008

(87) PCT Pub. No.: WO2007/107274
PCT Pub. Date: Sep. 27, 2007

(65) Prior Publication Data
US 2009/0070947 A1    Mar. 19, 2009

(30) Foreign Application Priority Data
Mar. 17, 2006 (EP) ................................. 06005512

(51) Int. Cl.
*H02P 1/00*      (2006.01)
*A63B 47/04*    (2006.01)
(52) U.S. Cl. .......... 318/119; 318/128; 15/21.1; 15/22.1; 15/33
(58) Field of Classification Search .................. 318/689, 318/119, 124, 128, 139, 291, 295, 514; 15/22.1, 15/21.1, 23, 38
See application file for complete search history.

(56) References Cited

U.S. PATENT DOCUMENTS

| 1,569,372 | A | * | 1/1926 | Horle ............................. 338/141 |
| 1,859,344 | A | * | 5/1932 | Ruben ............................ 338/142 |
| 2,292,425 | A | * | 8/1942 | Abrahamson ................. 338/161 |
| 2,468,144 | A | * | 4/1949 | Van Alen ....................... 338/218 |
| 3,324,440 | A | * | 6/1967 | Milton et al. ................. 338/162 |
| 3,343,115 | A | * | 9/1967 | Greenwood ................... 338/174 |
| 3,451,086 | A | * | 6/1969 | Burgett ............................ 15/23 |
| 4,081,782 | A | * | 3/1978 | Hildreth et al. ............... 338/200 |
| 4,185,263 | A | * | 1/1980 | Frey ............................... 338/301 |
| 4,647,897 | A | * | 3/1987 | Bingold et al. ............... 338/172 |
| 7,049,790 | B2 | * | 5/2006 | Pfenniger et al. ............ 320/114 |
| 7,721,371 | B2 | * | 5/2010 | Pfenniger et al. ............. 15/22.1 |
| 2006/0032512 | A1 | | 2/2006 | Kress et al. |

FOREIGN PATENT DOCUMENTS

| DE | 84 22 081 U1 | 10/1984 |
| EP | 1 584 263 A | 10/2005 |
| WO | WO 2005/077616 A1 | 8/2005 |

* cited by examiner

*Primary Examiner* — Walter Benson
*Assistant Examiner* — Thai Dinh
(74) *Attorney, Agent, or Firm* — Oliff & Berridge, PLC

(57) ABSTRACT

A toothbrush has a removable end cap at its free end area directed away from the bristles, which end cap closes off an inner space of a grip element. The end cap accommodates an electrical control element, in particular a potentiometer, which can be adjusted via an adjustment element arranged rotatably on the end cap. The toothbrush also comprises an electrical power consumption unit, in particular an electric motor, which is designed to set the bristles in vibration. The energy supply from an energy reservoir arranged in the interior to the electrical power consumption unit can be adjusted continuously by means of the control element, as a result of which the vibration intensity of the bristles can be steplessly adjusted.

32 Claims, 9 Drawing Sheets

ELECTRICALLY OPERATED, CONTINUOUSLY ADJUSTABLE PERSONAL HYGIENE DEVICE

The present invention relates to an electrically operated personal care device with the features of the precharacterizing clause of claim 1.

Such personal care devices are generally known. In WO 2005/046508, an electrically operated personal care device formed as a toothbrush is disclosed. The toothbrush has an electrical energy store, either a battery or a storage battery, which is arranged in an interior space in the grip body of the toothbrush. The grip body is adjoined by a neck region, which for its part goes over into a head region. Arranged in the head region is a care element with a covering of bristles. The covering of bristles is set in oscillation or vibration by an electric motor with a weight eccentrically mounted on the motor spindle. The motor is arranged in the neck region of the toothbrush. By means of an on/off switch arranged on the grip body, the motor can be connected to the energy store or disconnected from it. Furthermore, WO 2005/046508 discloses an electrical change-over switch, by means of which an additional resistor can be switched into the circuit. By inserting the additional resistor, the voltage across the motor drops, and as a result so does its rotational speed and consequently the intensity of the vibration.

An electrical operated personal care device formed as a razor is known from EP-A-1 563 967. This device is formed largely in analogy with the toothbrush disclosed in WO 2005/046508, but has in the head region a care element formed by an exchangeable razor head with a razor blade.

A disadvantage of the known, aforementioned personal care devices is found to be that the electrical power supplied to the electric motor cannot be influenced by the user, or only to a very restricted extent, whereby adaptation of the electrically operated personal care device to the respective individual needs of the user or to a technical configuration that is affected by tolerances is not possible, or only to a very restricted extent. This restricted adjustability of the personal care device can ultimately lead to inefficient use. For example, in the case of vibrational toothbrushes, there is no frequency that is optimum for all users. Users with sensitive gums are more likely to require a low-frequency massage, whereas other users would like a corresponding massage at moderate frequency. To achieve maximum cleaning performance, or a whitening effect, other users in turn require high-frequency cleaning. The same applies to rotating electric toothbrushes, only in this case the rotational frequency of the rotating brush part is adapted to the user's need. A rotating electric toothbrush is presented in DE-U-295 20 230.0.

The aim of the present invention is to provide an electrically operated personal care device which improves the efficiency of use and can consequently be adapted to the individual needs of the user.

This object is achieved by an electrically operated personal care device with the features of claim 1. Advantageous developments of the invention are provided by the dependent claims, the description and the drawing.

According to the invention, the electrically operated personal care device has a control device, which has an electrical control element which can be mechanically and manually set from the outside for continuously changing the energy flow between the energy store and the load and which ensures the functioning of the load as intended. As a result, it is possible to supply that amount of energy that is necessary for optimum use. This amount of energy may depend, inter alia, on the respective, individual components, such as for example on the electrical load and on the energy store, which respectively have internal tolerances caused by their production. Furthermore, it is ensured by the personal care device according to the invention that the load only uses energy when it is performing its function as intended. Furthermore, the personal care device also has a natural frequency, which is additionally influenced by the holding of the product in the user's hand (holding point, holding pressure). In general, the control device allows manual adjustment of the load.

Furthermore, in the case of a preferred embodiment, the amount of energy may depend on a care element that is driven by the load that is brought into a precisely defined state of excitation. Although every component can only be produced within certain tolerance limits, the continuous changeability of the energy flow from the energy store makes it possible to compensate for tolerances and to supply to said load the amount of energy required for optimum use, in particular also to operate the personal care device in resonance, that is to say with maximum oscillation.

According to a preferred embodiment, the care element is driven by the load. As a result, it is possible to influence exactly the energy supplied to the care element, in particular mechanical energy or thermal energy.

According to a further, preferred embodiment, the care element can be set in vibration and the intensity of the vibration can be set manually by means of the control element. This allows the vibration intensity to be set continuously by the respective user of the personal care device, steplessly in a range predetermined by the control element. In particular, a user can set the vibration intensity in such a way that the personal care device with the associated care element, in particular a care element covered with bristles, oscillates in resonance or that the settings correspond exactly to the personal needs of said user.

According to a further, preferred embodiment, the control element is a potentiometer, that is to say an electrical resistor that can be varied in a predetermined range. The mechanical, analogous formation of the control element means that very simple and low-cost production of the control element and of the personal care device is possible.

According to a preferred embodiment, the personal care device is formed as a toothbrush, in particular as a vibrational toothbrush—or rotating electric toothbrush, as a razor, in particular as a wet razor, or as a mascara applicator.

Examples of the invention are described below and represented in the drawings, in which purely schematically:

FIG. 1 shows by way of example an electrically operated personal care device 10 according to the invention, formed as a toothbrush 12. Other personal care devices such as other types of electric toothbrushes, electric wet razors or electric mascara applicators, may be analogously constructed.

Figure 1:
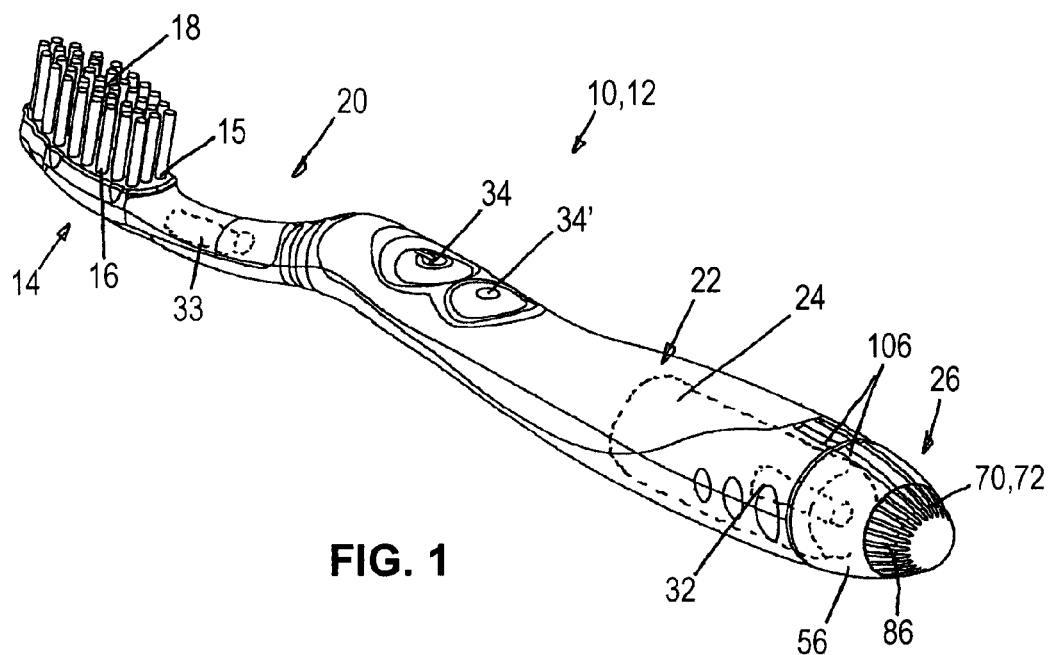
FIG. 1 shows a toothbrush according to the invention with an end cap, which contains a control element.

The toothbrush 12 has, arranged in a head region 14, a care element 16 formed as an exchangeable brush head with a bristle covering 18. The head region 14 is adjoined by a neck region 20 of the toothbrush 12, which is integrally connected to a grip body 22 of the toothbrush 12. The elongate grip body 22 has an interior space 24, which extends in the longitudinal direction of the latter and is accessible from the rear side of the grip body 22 opposite from the head region 14. Fitted on the grip body 22 from the rear side is an end cap 26, the connecting end region 28 of which (see FIG. 3) is inserted in the interior space 24. The end cap 26 is releasably held on the grip body 22 by means of a bayonet closure 30 (see FIG. 3 and FIG. 6). With the end cap 26 fitted on the grip body 22, the interior space 24 is closed in a watertight manner.

Arranged in the interior space 24 is an electrical energy store 32, which may be formed by a battery or by a storage battery. The energy store 32 is intended for supplying an electrical load 33, in the present case a motor with an eccentric oscillating element, with energy, which is intended for setting the head region 14 with the care element 16 in oscillation or in vibration. A switch arranged in the grip body 22, with an on button 34 and with an off button 34', serves the purpose of interrupting or closing the circuit (see FIG. 21) and is a component part of a control device of the toothbrush 12. Furthermore, the circuit can be interrupted by removing the end cap 26, achieving the effect that the toothbrush 12 can only be operated with the end cap 26 fitted on.

Figure 22:
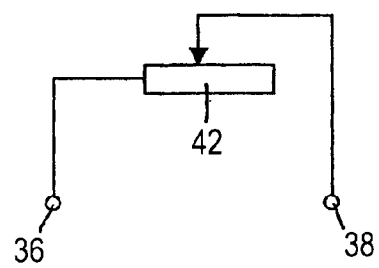
FIG. 22 shows the circuit diagram of the end cap.

The end cap 26, represented in FIG. 1 and in particular in FIGS. 3 to 6, has two contact elements 36, 38, which are electrically connected, or can be connected, to each other. The one contact element 36 is formed as a connecting pin 36', which lies in the axis of rotation of the bayonet closure 30. The other contact element 38 is formed as a contact strip 38', which is at right angles to the connecting pin 36' and is part of the bayonet closure 30. To establish the electrical contact between the grip body 22 and the fitted-on end cap 26, the grip body 22 has a counter-contact, which interacts with the contact strip 381 in a contact-making manner, and the energy store 32 has a contact element which is arranged in the axial direction of the bayonet closure 30 and interacts with the connecting pin 36' in a contact-making manner. In particular in the case of energy stores 32 that are used once, i.e. are not rechargeable (for example battery cells of sizes AA and AAA or so-called button cells), the connecting pin 36 acts directly on the energy store. The circuit diagram of the end cap 26 is shown in FIG. 22.

With the energy store 32 configured as a rechargeable storage battery, the toothbrush 12 has a socket lying in the interior space 24, near the opening of the latter, for the plugging in of a charger. The central pin of the socket also forms the contact element of the energy store 32 interacting with the connecting pin 36'. For charging the storage battery, the end cap 26 must consequently be removed, whereby the socket is exposed. This ensures that the circuit between the energy store 32 and the load is interrupted during the charging operation, whereby use of the toothbrush 12 is ruled out during this time. Consequently, as a result, unwanted ingress of water into the interior space 24 of the toothbrush 12 is prevented.

As described above, the toothbrush 12 is known from the international application with the publication number WO 2005/046508. For the precise construction of the toothbrush 12, in particular the forming of the neck region 20, the head region 14, the grip body 22 with the counter-contact arranged on it, the energy store 32 with the contact element, formed in particular with a storage battery, the arrangement of the electrical load and of the grip body as well as of the bayonet closure 30 formed on the end cap 26, you are referred to the cited publication. This publication likewise reveals which materials are used and how the production process proceeds. Furthermore, this publication reveals the circuit diagrams of the embodiment with a storage battery as the energy store, comprising a charging device for the storage battery.

As an alternative to the described charging technique by means of contact elements 36, 38 for the energy transmission, the known inductive charging may also be used. In this case, the end cap 26 is mounted only once and it is not necessary for the interior space 24 to be opened each time for the charging operation. As a difference from other toothbrushes, a charging coil for the inductive energy transmission is not located at the rear end of the grip body 22 but further forward in the grip in the direction of the head region 14. As shown in FIG. 1, the rear end is accommodated by the end cap 26 according to the invention.

FIG. 3 to FIG. 6 show various views and sectional representations of the end cap 26. This has externally the same contours, in particular in the connecting end region 28 (see FIG. 3), which is intended for engaging in the interior space 24 of the grip body 22, as the end cap disclosed in WO 2005/046508. For this reason, it can be exchanged without any problem for the end cap disclosed in WO 2005/046508, without having to make any adaptations to the existing device, in particular the toothbrush.

Figure 7:
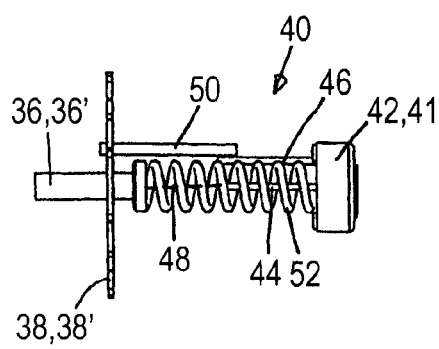
FIG. 7 shows the electrical subassembly of the end cap in elevation.
Figure 8:
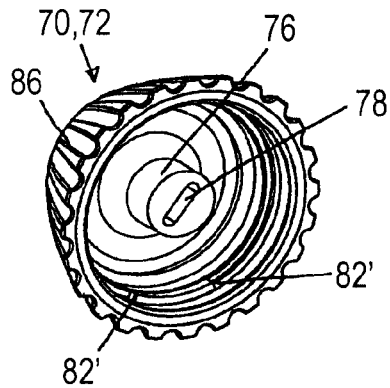
FIG. 8 shows a setting element formed as a rotary cap in a perspective representation.

An electrical subassembly 40 contained in the end cap 26 is shown in FIG. 7. The electrical subassembly 40 has a control element 41, formed as a rotary potentiometer 42, with two terminal pins 44, 46 projecting away to the same side from the housing part of the potentiometer 42. The one terminal pin 44 is led away centrally from the housing and the other terminal pin 46 is led away from a side region of the housing. The central terminal pin 44 is electrically connected to the connecting pin 36' via a litz wire 48, in order that the variability in the length of a helical spring 52 can be compensated. This helical spring 52 is intended for pressing the connecting pin 36' away from the potentiometer 46 in a spring-loaded manner, in order to ensure a good electrical connection directly with the contact element arranged in the grip body 22 or with the energy store. The other, lateral terminal of the potentiometer 42 is electrically connected to the contact strip 38' via a contact pin 50; the contact strip is arranged at right angles to the connecting pin 36'. The connecting pin 36' is led through a centrally arranged through-opening in the contact strip 38', the diameter of the connecting pin 36' being chosen to be smaller than the diameter of the through-opening (see FIG. 5). The two contact elements 36 and 38 are insulated with respect to each other or at least spaced apart sufficiently that no short-circuit between the contact elements 36, 38 can take place when the circuit is closed by fitting the end cap 26 onto the grip body 22.

Also arranged between the connecting pin 36' and the potentiometer 42 is a helical spring 52, acting as a compression spring, which is passed through centrally by the litz wire 48 and the terminal pin 44. To prevent mechanical loading, in particular abrasion, on the housing of the potentiometer 42 by the helical spring 52, provided between the potentiometer 42 and the spring 52 is a shim, which may be formed by an electrically conducting or insulating material.

The circuit diagram associated with the electrical subassembly 40 is shown in FIG. 22. It can be seen from this that the potentiometer 42 is electrically connected on the one hand to the contact element 36 and on the other hand to the contact element 38. It goes without saying that differently configured, electrically conducting contact elements may also be chosen. Preferably, however, the contacting with respect to the grip body 22 takes place in a region that is sealed off from the outside world.

Figure 21:
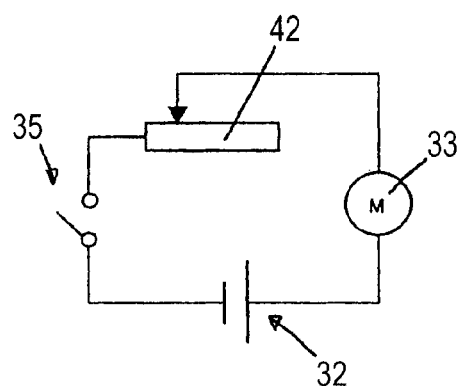
FIG. 21 shows the electrical circuit diagram of the electrically operated personal care device.

The circuit diagram of the toothbrush formed with a battery that is used once (disposable battery) or a rechargeable storage battery as the energy store 32 is shown in FIG. 21. The one pole of the energy store 32 is connected to the one terminal pin of the potentiometer 42 via the on/off switch 35, which has the on button 34 and off button 34' shown in FIG. 1. The other terminal pin of the potentiometer 42 is connected to the other pole of the energy store 32 via the electrical load 33.

In the case of the circuit diagrams represented in FIGS. 21 and 22, the electrical elements contained in the circuit diagram are preferably connected in series. With the device switched on, the current flow is directed permanently via the potentiometer. Consequently, the resistance of the potentiometer at maximum power of the load is preferably close to 0Ω (ohms).

Figure 9:
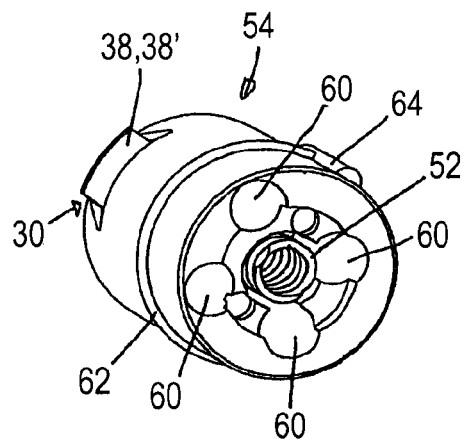
FIG. 9 shows a core part with a contact strip and a spring inserted in it in a perspective representation.
Figure 10:
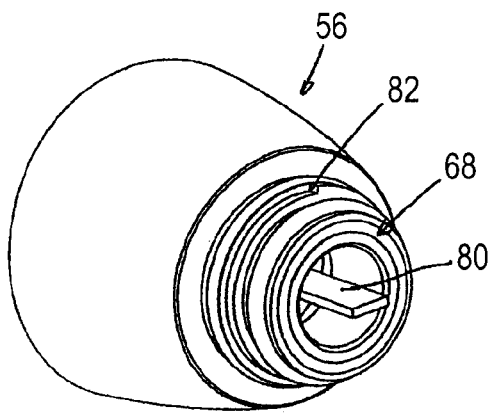
FIG. 10 shows a shell part of the end cap in a perspective representation, a driver being visible inside the axial opening.

The elements of the electrical subassembly 40 are fitted in a core part 54, shown in particular in FIG. 9, of the end cap 26 (see FIGS. 3 to 6) and fixed by a shell part 56, shown in particular in FIG. 10, of the end cap 26, which is fitted on the core part 54.

The core part 54, shown in particular in FIG. 9, with the fitted-in helical spring 32 and contact strip 38', is formed substantially as a circular cylinder. That end region of the core part 54 which holds the contact strip 38' in a radial, dovetail-shaped groove, forms the connecting region 28 of the end cap 26 that can be inserted into the grip region 22. The contact strip 38' projects on both sides beyond the lateral surface of the core part 54 and serves on the one hand as a contact element 38 and on the other hand as an engaging element of the bayonet closure 30, which interacts with the likewise conductingly formed counter-contact, formed on the grip body 22, of the bayonet closure 30. Extending centrally and in the direction of the axis of the cylinder, the core part 54 has a through-opening, in which the helical spring 52 is guided. The through-opening has on the one hand, in the connecting region 28, a step-like taper 58, which forms a stop for a plate-shaped head of the connecting pin 36'. On the other hand, the through-opening widens in a step-like manner to a diameter that corresponds substantially to that of the potentiometer 42, so that the latter can be fitted into the widened region. Parallel to the through-opening, the core part 54 has four lateral blind openings 60. In one of these four lateral blind openings 60 there is at the bottom a through-hole, through which the lateral terminal pin 46 and the contact pin 50 are led through the core part 54. The lateral blind openings 16 serve in particular for saving material and for minimizing the production time (cycle time) of the core part 54, which is preferably produced from plastic.

As FIG. 9 shows, the core part 54 laterally has a peripheral bead 62 and a longitudinally aligned guide bead 64, which are intended for holding the shell part 56 on the core part 54 by means of a snap connection or for fixing the position of the shell part 56 with respect to the core part 54 in the circumferential direction. The peripheral bead 62 may be formed both as a hard component and as a soft component or an O-ring. The soft component would be molded on directly during production as a further component. The use of the soft component or the O-ring additionally seals the device from water. Possible materials for the soft component and for the hard component are given further below.

The shell part 56 is fitted on the core part 54 and connected to it by means of the snap connection. For this purpose, the shell part 56 has a groove 66 interacting with the peripheral bead 62 of the core part 54. To define the position of the shell part 56 in the circumferential direction with respect to the core part 54, the shell part 56 has a guide recess interacting with the guide bead 64.

Figure 6:
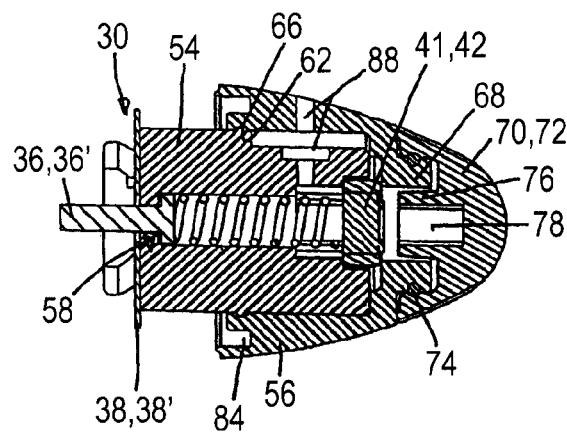
FIG. 6 shows the end cap in sectional representation.
Figure 11:
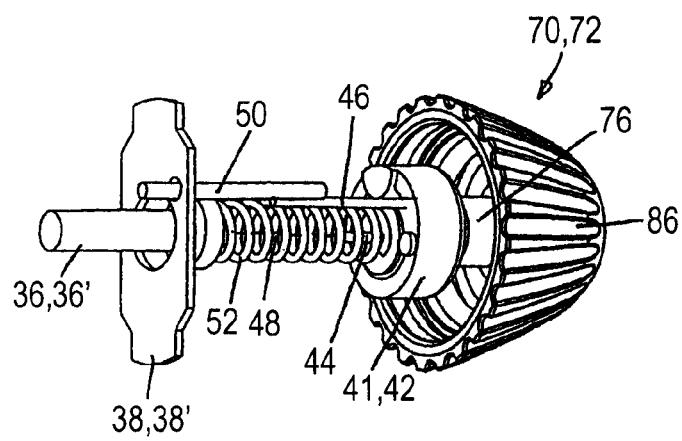
FIG. 11 shows the electrical subassembly shown in FIG. 7 in a perspective representation, with the setting element shown in FIG. 8.

In the interior, the shell part 56 has—see in particular FIG. 6—a stepped, cylindrical recess. The diameters of the stepped recess are chosen such that the shell part 56 can be fitted snugly onto the core part 54 and the potentiometer 42 is clamped in between stop faces formed on the core part 54 and on the shell part 56. To define the position of the potentiometer 42 in its circumferential direction, the potentiometer 42 has a projection (see FIG. 11), which engages in a depression of the core part 54 that is formed between the lateral blind openings 60. As a result, the potentiometer 42 can be exactly positioned and secured against twisting. It must be ensured in particular that this anti-twist locking is chosen with respect to the housing of the potentiometer 42 and not with respect to the fragile electrical terminal pins 44, 46.

Furthermore, the shell part 56 has a circular-cylindrical hollow cylinder continuation 68 (see FIGS. 6 and 10). The setting element 72, formed as a rotary cap 70, is rotatably fitted on the latter. The axis of the hollow cylinder continuation 68 is congruent with the axis of rotation of the setting element 72 and the axis of rotation of the potentiometer 42 as well as the axis of the connecting pin 36'. The outer lateral surface of the hollow cylinder continuation 68 has a peripheral groove, in which an O-ring 74 is placed or integrally molded, serving on the one hand as a sealing element and on the other hand as a fastening element in the axial direction for the setting element 72. If integrally molded, this O-ring would preferably again be integrally molded with other elements, for example haptic elements, of a soft component on the setting element 72 or hollow cylinder continuation 68. This also applies to all other O-rings or other sealing elements discussed in this document.

The setting element 70, 72 is fitted on the hollow cylinder continuation 68. The setting element 70 has a peripheral groove, which interacts with the O-ring 74 arranged on the hollow cylinder continuation 68. This groove and the groove 66 are preferably forcibly demolded during the injection-molding process.

The setting element 72 also has a central continuation 76, which protrudes into the hollow cylinder continuation 68 and has a slot-like receptacle 78. A flat profile-like driver 80 (only shown in FIG. 10) is fitted on the one hand in the receptacle 78 of the setting element 72 and on the other hand in a driver recess of the potentiometer 42. This mechanical connection of the potentiometer 42 to the rotary cap 70 or the setting element 72 allows the potentiometer 42, forming a control element 41, to be set from the outside.

Furthermore, the hollow cylinder continuation 68 has on its outer lateral surface two stop faces 82, which are shown in FIG. 10, interact with counter stop faces 82' on the setting element 72, and thereby define a rotary range of the setting element 72. The stop faces 82 together with the counter stop faces 82' form a setting limitation. This prevents over-turning of the setting element 72 and at the same time defines a setting range in which the setting of the control element 72 may lie. It is generally proposed in the case of all the configurational variants to define the setting range of the potentiometer 42 by means of stops on elements of the device, although customary potentiometers on the market may already have stops.

The setting element 72 is preferably rotatable with respect to the shell part 56 from a defined 0° position over an angle range of up to 350°; an angle range of between 150° and 270° is particularly preferred. The start and end points of the rotary scale are preferably placed on an axis of symmetry of the end cap 26. The intensity of the load is preferably increased by turning to the right and reduced in the opposite direction.

The shell part 56 has on the end face, facing the connecting end region 28 of the end cap 26, a peripheral groove 84. With the end cap 26 fitted on the grip body 22 (see FIG. 1), a bead arranged on the end face of the grip body 22 engages in this groove 84. In order that no water can get into the interior space 24, a sealing element is preferably placed in the groove 84. It goes without saying that the sealing element may also be integrally molded on the shell part during the production of the latter, preferably with the production of other sealing elements or haptic elements of a soft component on the shell part 56.

The outer form of the shell part 56 is made to match the outer form of the grip body 22 in such a way that, with the end cap 26 fitted on, a continuous transition between the shell part 56 and the grip body 22 is formed, cross-sectional areas not having to be rotationally symmetrical.

The mounting of the shell part 56 on the grip body 22 is ensured by the circular groove 84 on the shell part 56 and a circular bead protruding from the grip body 22 and engaging in the groove 84, which at the same time also makes optimum sealing possible.

The setting element 72 has a preferably rotationally symmetrical outer form. To ensure a continuous transition between the shell part 56 and the setting element 22 in every rotational position, the shell part 56 likewise has a rotationally symmetrical outer form adjoining the setting element 72.

Figure 3:
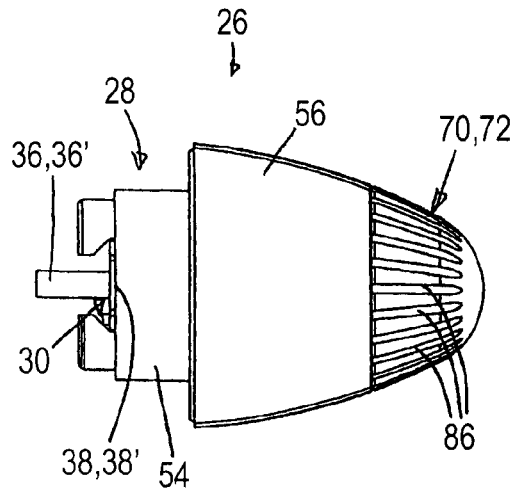
FIG. 3 shows the end cap in side view.
Figure 5:
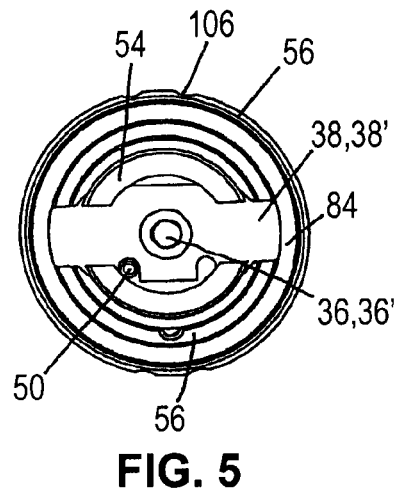
FIG. 5 shows the end cap in rear view, the central contact and the lateral contacts being visible in particular.
Figure 4:
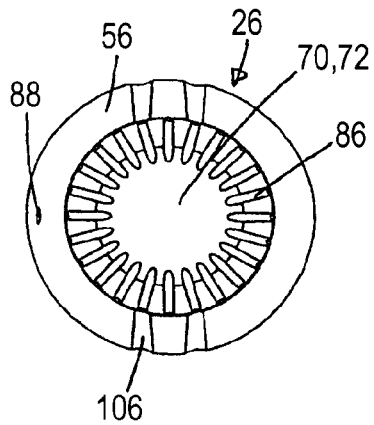
FIG. 4 shows the end cap in front view.

Furthermore, the surface of the setting element 72 is provided with furrows 86 or other haptic elements such as nubs, scales, rings or the like of a hard component, soft component or a combination thereof (see FIGS. 3, 4, 8 and 11), in order to improve its grip. The setting element 72 may have a rounded-off form, as shown in FIGS. 3 and 6. As an alternative, the setting element 72 may also have a flat termination, in order that the device can be placed vertically on this flat termination when not in use. Furthermore, the surface of the shell part 56 is provided with markings 106, for example channels, numbers, symbols or the like, which are continued in the grip body 22 (see FIGS. 4, 5 and in particular FIG. 1). These markings may also be printed on or injection-molded from a combination of a soft component and a hard component. As a result, the desired positioning of the fully fitted-on end cap 26 with respect to the grip body 22 can be clearly seen.

A force to be exerted to release the bayonet closure 30 is much greater than the force to be exerted to turn the setting element 72. The torque required to open the bayonent closure 30 is preferably at least 10%, preferably 30%, greater than the torque required to turn the setting element 72. It must be ensured in the case of all the solution variants that the anti-twist locking of the potentiometer 42 is chosen to be sufficiently strong that the end cap 26 could, if need be, also be opened by turning the setting element 72 against the stop arranged on the shell part 56 or optionally a stop of the potentiometer 42.

In the radial direction, the shell part 56, and also the core part 54, has a venting clearance 88, which is arranged congruently in the assembled state of the end cap 26, so that, in the case of gases escaping from the energy store 32, in particular when a storage battery is used as the energy store, they can escape from the interior space 24 through the end cap 26. A membrane (not shown) is also arranged in the venting clearance 88, so that no water can get into the interior of the end cap 36, but the gases can escape from the interior space 24 and the end cap 26. The membrane is preferably adhesively attached to the core part 54 and kept away from the shell part 56 in such a way that the membrane is not touched by the shell part 56, and consequently damaged, when the shell part 56 is mounted onto the core part 54. The venting clearance 88 of the core part 54 is to be formed accordingly. If a disposable battery is used as the energy store, it is possible to dispense entirely with the venting clearance 88 in the shell part 56 and in the core part 54.

Used with preference as the material for the core part 54, the shell part 56 and for the setting element 52 is a hard plastic, for example a hard component such as for example polypropylene (PP), polyester (PET), polyethylene (PE), polystyrene (PS), styrene acrylonitrile (SAN), polyoxymethylene (POM), polymethylmethacrylate (PMMA), acrylonitrile butadiene styrene (ABS), polycyclohexane dimethanol terephthalate (PCT/PCT-A (acid-modified)/PCT-G (glycol-modified)) and polyamide (PA), with polypropylene (PP) preferably being used. The modulus of elasticity of polypropylene preferably lies between 1000 N/mm$^2$ and 2400 N/mm$^2$ and, with particular preference, between 1300 N/mm$^2$ and 1800 N/mm$^2$. The parts mentioned that are produced from plastic may also comprise a number of hard components, which serve in particular for the visual design of the parts. Furthermore, said parts may also be provided with additional soft components.

The setting element 72, and also the shell part 56, may also have areas or elements of a soft component on its outer surface, whereby the haptic or the grip can be improved. As already mentioned, the sealing ring and the O-ring are likewise produced from a soft component. Low-density polyethylene (PE-LD), high-density polyethylene (PE-HD), polyethylene (PE), a rubber-elastic material such as polyurethane (PU), a thermoplastic elastomer (TPE) or polyvinyl chloride (PVC) is used for example as the soft component, with a thermoplastic elastomer (TPE) being used with preference. The Shore A hardness of the thermoplastic elastomer preferably lies below 90. The soft component is integrally molded onto the hard component in an injection-molding operation preferably following directly after the injection-molding operation for the hard component. The parts are preferably produced from two or more polymer components by the multi-component injection-molding process.

The electrically conducting parts, such as the contact elements 36, 38, litz wire 48, shim, contact pin 50 and sheet-metal part 100, are preferably produced from a stainless, surface-treated or improved metal, in order that the electrical conduction works satisfactorily.

The end cap 26 of the electrically operated personal care device 10 according to the invention is mounted as follows:

Firstly, the contact strip 381 is inserted into the core part 54. After that, the lateral terminal pin 46 of the potentiometer 42 is widened by the contact pin 50, the connection preferably being made here by soldering. Furthermore, the shim is arranged on the side of the terminals of the potentiometer 42 and the litz wire 48 is attached in an electrically conducting manner to the central terminal pin 44 of the potentiometer 42. After that, the spring 52 is pushed over the litz wire 48 and the central terminal pin 44. Then, the connecting pin 26' is placed with its plate-shaped end on the helical spring 52, and connected in a conducting manner to the litz wire 48. In the next-following step, the potentiometer 42 is inserted with the parts connected to it in a conducting manner into the core part 54 and the contact pin 50 is connected in an electrically conducting manner to the contact strip 38'. After that, the shell part 56 is fitted onto the core part 54, the shell part 56 thereby being guided by the guide bead 64 and the peripheral bead 62 of the core part 56 latching into the peripheral groove 66 of the shell part 56. Furthermore, the O-ring 74 is fitted into the groove on the hollow cylinder continuation 68, unless it has been integrally molded onto the shell part 56 directly during the production of the latter. Furthermore, the driver 80 is fitted into the recess of the setting element 72 and the setting element 72 is fitted together with the driver 80 onto the shell part, correct insertion of the driver 80 into the driver receptacle 78 of the potentiometer 42 having to be ensured.

Those parts that lie in series in the circuit are preferably connected in an electrically conducting manner, that is to say they are soldered, pressed, riveted, adhesively attached, etc. This ensures the electrical connection of the parts, since, without connection, the parts can otherwise slip, or dust and/or dirt particles can get into the connection and this could cause the circuit to be interrupted.

Figure 40:
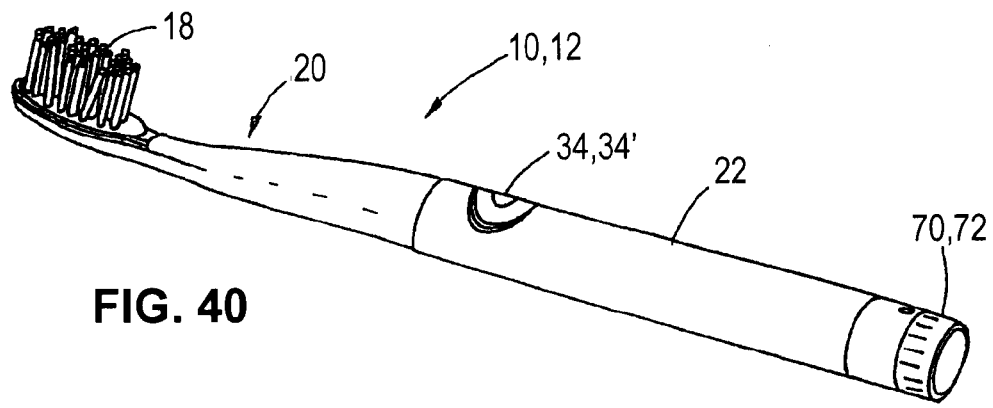
FIG. 40 shows a further embodiment of an electric toothbrush according to the invention in a perspective view, with a setting element in the end cap.
Figure 41:
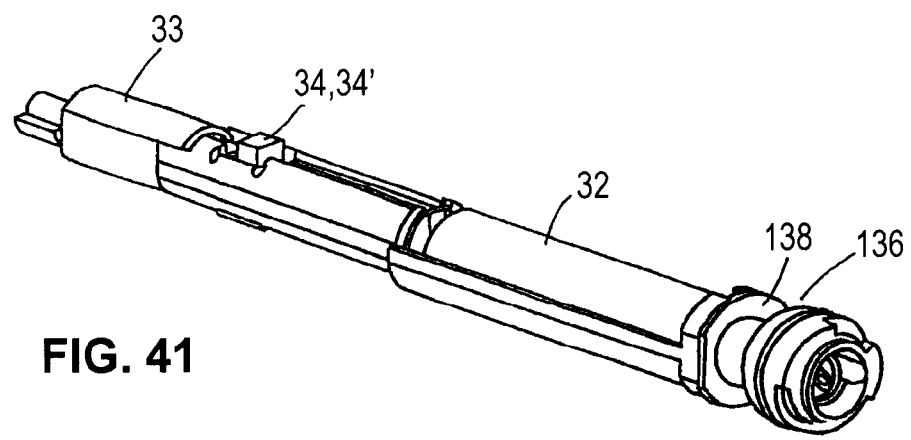
FIG. 41 shows internal workings of the embodiment shown in FIG. 40 of the electric toothbrush in a perspective view.
Figure 42:
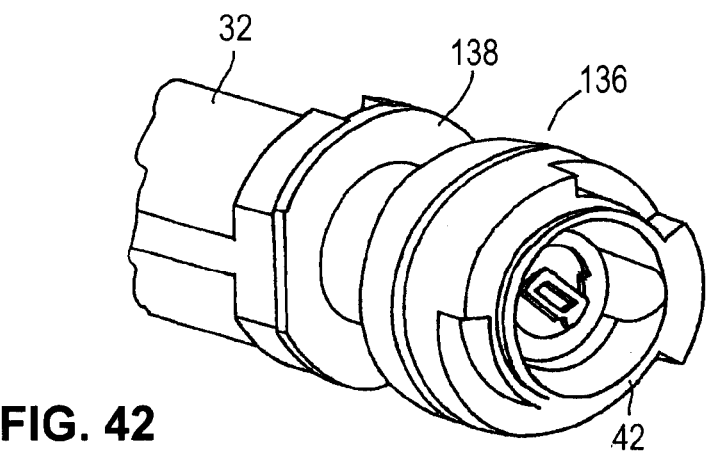
FIG. 42 shows a detail of the internal workings shown in FIG. 41 in a perspective view, with a potentiometer integrated in a coil carrier.

As an alternative, the potentiometer 42 may be provided on a carrier unit of the electric toothbrush 12, so that the adjustment can still be made at the end of the toothbrush 12, see FIG. 40, FIG. 41 and FIG. 42. The end cap 26 can no longer be removed. As represented in FIGS. 41 and 42, the potentiometer 42 is arranged in a coil carrier 136. The coil (not represented in the figures) is provided in a preferably peripheral coil recess 138. The coil is responsible for the inductive charging of the toothbrush 12 in a charging station and lies in front of the potentiometer 42 in the direction of the head region 14, that is to say not at the free end of the grip body 22. The circuit connects the various electrical components and leads through the potentiometer 42, which is attached to the free end region of the electric toothbrush 12. The housing of the toothbrush 12 is flattened off at the rear free end, so that it can be put down on it. The coil carrier 136 is formed in one piece. The functions and the setup of the potentiometer 42 are analogous to those described above.

Figure 12:
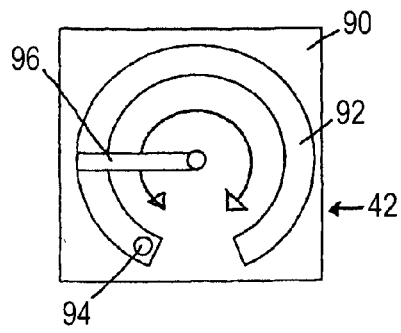
FIGS. 12-20 show various control elements formed as potentiometers.

FIG. 12 shows a first embodiment of the potentiometer 42 (without the housing of the potentiometer) in a plan view. The potentiometer 42 has a non-conducting carrier 90 of ceramic or hard paper, on which a conducting part-arc 92 has been applied. The part-arc 92 is formed for example by a carbon compound, a Ceramed or cermet, from a radially wound resistance wire or from a conductive plastic. The part-arc 92 forms the resistor and is electrically connected to a stationary, first contact 94, which is electrically connected for example to the lateral terminal pin 46 of the potentiometer 42. Furthermore, the potentiometer 42 has a rotatable, electrically conducting tap 96, which is on the one hand supported in a contact-making manner on the part-arc 92 and on the other hand is connected at the rotary center of the tap 96 to a second contact, which is electrically connected for example to the central terminal pin 44 of the potentiometer 42. The potentiometer 42 preferably has a turning limitation at both ends of the part-arc 92, so that the tap 96 can only be moved or turned on the part-arc. Since the end cap 26 already has a turning limitation, formed by the stop faces 82 and the counter stop faces 82', however, it is possible to dispense with the turning limitation on the potentiometer 42.

Figure 13:
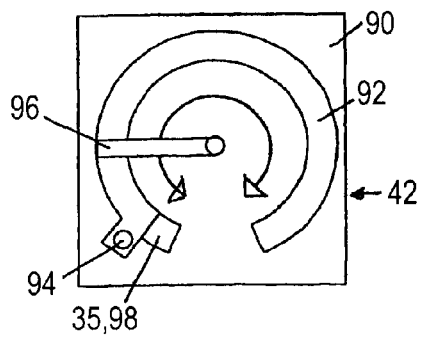

A further embodiment of the potentiometer 42, shown in FIG. 13, has an additional on/off switch, which is formed by a non-conducting end region 98 of the part-arc 92. The positioning of the tap 96 on the non-conducting end region 98 interrupts the circuit between the contact 24 and the tap 96. With the first contact 94, the end region 98 adjoins the part-arc, the first contact 94 being offset radially outward, in this embodiment laterally. Consequently, when a potentiometer 42 is used, as shown in FIG. 13, it is possible to dispense with the on/off switch 34, 34' (see FIG. 1) in the grip body 22 of the toothbrush 12.

Figure 14:
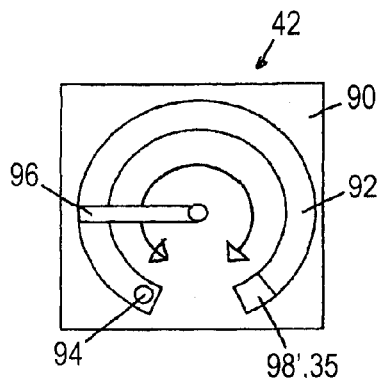

A further embodiment of the potentiometer 42 is shown in FIG. 14. As a difference from the one shown in FIG. 13, this potentiometer 42 has the non-conducting end region 98', adjoining the part-arc 92 at the opposite end in the circumferential direction. This has the consequence that the on/off switch is arranged so as to connect to the maximum resistance of the potentiometer. By contrast with this, the on/off switch of the potentiometer 42 shown in FIG. 13 is arranged so as to connect to the minimum resistance of the potentiometer.

Figure 15:
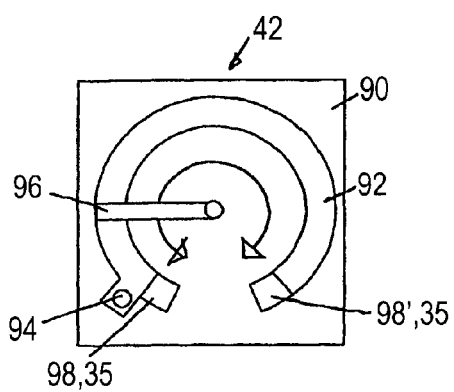

A further embodiment of the potentiometer 42, which represents a combination of the potentiometers 42 according to FIG. 13 and FIG. 14, is shown in FIG. 15. This potentiometer 42 has a non-conducting end region 98, 98' on both sides in the circumferential direction of the part-arc. As a result, the potentiometer 42 has an on/off switch connecting to the maximum resistance region and the minimum resistance region.

The resistance characteristic of the potentiometer 42, in particular its maximum resistance, is to be made to match the control device used in the grip body 22 and the electrical load 33, so that the functioning of the load 33 as intended is ensured. In the present exemplary embodiment of the electric toothbrush 12 and in the following exemplary embodiments of a wet razor and a mascara applicator, the electrical load is an electric motor, which requires a certain minimum voltage for starting of approximately 0.3 V to 0.6 V and, accordingly a corresponding starting current. The maximum voltage drop across the potentiometer 42 or across the control device consequently must not lead to a voltage below the minimum voltage across the electrical load, since otherwise the latter will not work (current less than the starting current), but nevertheless use up current, and consequently not function as intended. Preferably, the maximum possible voltage drop across the potentiometer is set such that, even with a partially discharged, weaker energy store 32, the minimum operating voltage of the load 33 is still reached.

A minimum resistance of the potentiometer 42 used preferably lies close to 0Ω. The maximum resistance preferably lies around 1 MΩ. With particular preference, a resistance of between 1Ω and 50Ω may be set with the potentiometer 42.

The potentiometer 42 is designed for allowing a current with a current intensity of between 0.01 A and 4 A to flow. Preferably, a current of the intensity from 0.05 A to 1 A flows.

The following table provides information on the required electrical design of various loads; various discrete examples are given:

|  | Voltage in volts | Current in amperes | Minimum voltage | Potentiometer Resistance in ohms | Max. current loading | Power in watts | Addition 1 | Addition 2 |
|---|---|---|---|---|---|---|---|---|
| Vibrational toothbrush | 1.25 | 0.1-0.8 | 0.4 | 3.0-25 | 0.8 | 0.03-0.25 | | |
| | 1.5 | 0.1-1.0 | 0.4 | 4.0-45 | 1 | 0.04-0.75 | | |
| | 2.5 | 0.1-0.5 | 0.6 | 15-80 | 0.5 | 0.06-0.35 | | |
| | 3 | 0.1-0.6 | 0.7 | 15-100 | 0.6 | 0.15-0.5 | | |
| | 4.2 | 0.05-0.4 | 0.9 | 35-250 | 0.4 | 0.06-0.5 | | |
| | 4.5 | 0.05-0.5 | 0.9 | 30-360 | 0.5 | 0.06-0.6 | | |
| Rotational toothbrush | 1.25 | 0.3-1.2 | 0.7 | 0.7-3.0 | 1.2 | 0.1-0.4 | | |
| | 1.5 | 0.3-1.2 | 0.7 | 1.0-5.0 | 1.2 | 0.15-0.5 | | |
| | 2.5 | 0.15-0.8 | 0.9 | 5.0-30 | 0.8 | 0.1-0.5 | | |
| | 3 | 0.15-0.8 | 0.9 | 8.0-45 | 0.8 | 0.12-0.6 | | |
| | 4.2 | 0.15-0.6 | 1.2 | 15-75 | 0.6 | 0.2-0.7 | | |
| Vibrational wet razor | 1.25 | 0.1-0.8 | 0.4 | 3.0-25 | 0.8 | 0.03-0.25 | | |
| | 1.5 | 0.1-1.0 | 0.4 | 4.0-45 | 1 | 0.04-0.75 | | |
| | 2.5 | 0.1-0.5 | 0.6 | 15-80 | 0.5 | 0.06-0.35 | | |
| | 3 | 0.1-0.6 | 0.7 | 15-100 | 0.6 | 0.15-0.5 | | |
| | 4.2 | 0.05-0.4 | 0.9 | 35-250 | 0.4 | 0.06-0.5 | | |
| Mascara applicator | 1.25 | 0.5-1.0 | 0.6 | 1.5-3.0 | 1 | 0.15-0.35 | | |
| | 1.5 | 0.4-0.8 | 0.7 | 2.0-5.0 | 0.8 | 0.15-0.35 | | |
| | 2.5 | 0.25-0.5 | 0.9 | 10.0-20.0 | 0.5 | 0.2-0.4 | | |
| | 3 | 0.2-0.4 | 1.2 | 15.0-30.0 | 0.4 | 0.15-0.3 | | |
| | 4.2 | 0.15-0.3 | 1.5 | 23.0-50.0 | 0.3 | 0.2-0.4 | | |
| LED/OLED | 1.25 | 0.01-0.05 | 0.9 | 10-100 | 0.05 | 0.01-0.05 | with electronics | |
| | 1.5 | 0.01-0.05 | 0.9 | 10-100 | 0.05 | 0.01-0.05 | with electronics | |
| | 2.5 | 0.01-0.05 | 2 | 10-100 | 0.05 | 0.01-0.05 | | |
| | 3 | 0.01-0.05 | 2 | 25-150 | 0.05 | 0.02-0.06 | | |
| | 4.2 | 0.01-0.05 | 2 | 50-250 | 0.05 | 0.03-0.12 | | |
| Fluid pump | 1.25 | 0.3-1.0 | 0.9 | 0.5-2.0 | 1 | 0.1-0.4 | | |
| | 1.5 | 0.3-1.0 | 1 | 0.75-2.5 | 1 | 0.15-0.4 | | |
| | 2.5 | 0.15-0.5 | 1.2 | 6.0-20 | 0.5 | 0.1-0.4 | | |
| | 3 | 0.15-0.5 | 1.2 | 10.0-50.0 | 0.5 | 0.15-0.4 | | |
| | 4.2 | 0.1-0.25 | 1.8 | 25.0-60.0 | 0.25 | 0.15-0.3 | | |
| Loudspeaker | 1.25 | 0.04-0.35 | 0.4 | 10.0-70.0 | 0.35 | 0.02-0.15 | 4-32 ohms | |
| | 1.5 | 0.05-0.4 | 0.4 | 10.0-100 | 0.4 | 0.02-0.15 | 4-32 ohms | |
| | 2.5 | 0.08-0.35 | 0.4 | 50.0-200 | 0.35 | 0.05-0.25 | 8-32 ohms | |
| | 3 | 0.1-0.4 | 0.4 | 50.0-250 | 0.4 | 0.1-0.3 | 8-32 ohms | |
| | 4.2 | 0.04-0.4 | 0.4 | 100-1000 | 0.4 | 0.05-0.5 | 10-100 ohms | |
| Magnetic field | 1.25 | 0.04-0.35 | 0.4 | 10.0-70.0 | 0.35 | 0.02-0.15 | 4-32 ohms | |
| | 1.5 | 0.05-0.4 | 0.4 | 10.0-100 | 0.4 | 0.02-0.15 | 4-32 ohms | |
| | 2.5 | 0.08-0.35 | 0.4 | 50.0-200 | 0.35 | 0.05-0.25 | 8-32 ohms | |
| | 3 | 0.1-0.4 | 0.4 | 50.0-250 | 0.4 | 0.2-0.3 | 8-32 ohms | |
| | 4.2 | 0.04-0.4 | 0.4 | 100-1000 | 0.4 | 0.05-0.5 | 20-100 ohms | |
| Electric field | 1.25 | 0.25-1.2 | 0.9 | 0.4-2.0 | 1.2 | 0.1-0.4 | with electronics | 0.3-1.5 watts |
| | 1.5 | 0.2-1.0 | 1 | 1.0-5.0 | 1 | 0.1-0.4 | with electronics | 0.3-1.5 watts |
| | 2.5 | 0.12-0.6 | 1.2 | 7.0-25 | 0.6 | 0.1-0.4 | with electronics | 0.3-1.5 watts |
| | 3 | 0.1-0.5 | 1.2 | 10.0-50 | 0.5 | 0.1-0.4 | with electronics | 0.3-1.5 watts |
| | 4.2 | 0.07-0.36 | 1.8 | 20.0-100 | 0.36 | 0.1-0.4 | with electronics | 0.3-1.5 watts |

-continued

| | | | | Potentiometer | | | | |
|---|---|---|---|---|---|---|---|---|
| | Voltage in volts | Current in amperes | Minimum voltage | Resistance in ohms | Max. current loading | Power in watts | Addition 1 | Addition 2 |
| Thermal radiation | 1.25 | 0.5-1.0 | 0.6 | 1.5-3.0 | 1 | 0.15-0.35 | | |
| | 1.5 | 0.4-0.8 | 0.7 | 2.0-5.0 | 0.8 | 0.15-0.35 | | |
| | 2.5 | 0.25-0.5 | 0.9 | 10.0-20.0 | 0.5 | 0.2-0.4 | | |
| | 3 | 0.2-0.4 | 1.2 | 15.0-30.0 | 0.4 | 0.15-0.3 | | |
| | 4.2 | 0.15-0.3 | 1.5 | 25.0-50.0 | 0.3 | 0.2-0.4 | | |
| EL film (electro-luminescent film) | 1.25 | 0.3-1.0 | 0.9 | 1.2-5 | 1.0 | 0.05-0.35 | with electronics | |
| | 1.5 | 0.25-0.8 | 0.9 | 1.6-6 | 0.8 | 0.05 0.35 | with electronics | |
| | 2.5 | 0.15-0.5 | 1.1 | 5-20 | 0.5 | 0.05-0.35 | with electronics | |
| | 3 | 0.13-0.4 | 1.3 | 7.5-25 | 0.4 | 0.05-0.35 | with electronics | |
| | 4.2 | 0.1-0.3 | 2.0 | 12-45 | 0.3 | 0.05-0.35 | with electronics | |
| | 4.5 | 0.09-0.27 | 2.1 | 15-50 | 0.27 | 0.05-0.35 | with electronics | |
| Blade heating | 1.25 | 0.05-0.25 | 0.4 | 2.0-20 | 0.25 | 0.02-0.15 | | |
| | 1.5 | 0.05-0.30 | 0.4 | 2.0-25 | 0.3 | 0.02-0.15 | | |
| | 2.5 | 0.025-0.125 | 0.8 | 20-100 | 0.125 | 0.02-0.15 | | |
| | 3.0 | 0.015-0.10 | 0.8 | 25-200 | 0.1 | 0.02-0.15 | | |
| | 4.2 | 0.012-0.075 | 1.0 | 50-350 | 0.075 | 0.02-0.15 | | |
| | 4.5 | 0.01-0.07 | 1.2 | 60-500 | 0.07 | 0.02-0.15 | | |

To explain the individual columns: voltage in volts indicates the size of the supply voltage, i.e. the voltage of the fully charged energy store. Current in amperes indicates the maximum current intensity in the circuit for the respective application. Minimum voltage refers to the voltage that is the least required to operate the load/make it work. Under potentiometer, the individual characteristic values of the potentiometer 42 are indicated; they are so-called mechanical variables of the potentiometer 42. Resistance in ohms indicates the maximum overall resistance of the potentiometer 42, i.e. the potentiometer 42 can be regulated in the range from close to 0 ohms up to the value specified (influenced by the minimum voltage). The maximum current loading indicates the size of the maximum current intensity that the potentiometer 42 withstands. The power in watts indicates the size of the power consumption of the potentiometer 42. Under addition 1, various data on the various loads are indicated. With the LED, it is indicated which ones still require electronics (i.e. a converter, etc.) to operate them; this is already included in the calculation of the figures. With the loudspeakers, the resistance ranges of the possible loudspeakers are indicated. With the magnetic field, the possible resistances of the coil that generates the magnetic field are listed. With the electric field, it is indicated under addition 1 that a converter is needed in each case to generate the electric field. Under addition 2, the power of the converter is indicated.

The additional applications described in the table, such as for example the loudspeaker or the thermal radiation, are conceivable on all personal care devices that are equipped with a control element according to the invention.

To ensure the greatest possible ease of handling and ergonomics and to be able to accommodate the potentiometer 42 in a closure, smallest possible installation dimensions and weight of the component must be ensured. For this reason, a potentiometer 42 has a weight of less than 10 g, preferably less than 2 g. The volume of the potentiometer 42, without projecting contacts, is preferably chosen to be less than 10,000 mm$^3$, in particular less than 1000 mm$^3$.

The rotary range of the potentiometer 42 is adapted to the rotary range/angle range of the setting element 72 and limited by the limitations provided on the setting element 72.

In a further embodiment of the end cap 26, markings which indicate and/or fix the setting of the control element or the setting element 72 are provided. Such markings may be simple lines, widening lines, a line widening from minimum to maximum, "min" and "max", "on" and "off" or "massage" and "cleaning" or any combination of such markings, in order that the position of the setting, i.e. the intensity, can be visually established. These markings are provided directly during the production of the setting element 72 and the shell part 56 and may consist either of a soft component, a hard component or of a combination. Furthermore, such markings may also be applied by printing or stamping. Furthermore, mechanical latching elements may be provided on the setting element 72 and on the shell part 56, so that the relative position of the setting element 72 with respect to the shell part 56 can be heard and/or can be felt. An intensity of the audible or feelable latching engagement may be created in dependence on the set resistance and the resultant intensity of the load 33.

Figure 23:
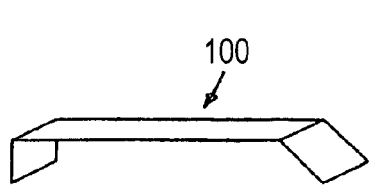
FIGS. 23 and 24 show two differently formed contact elements.
Figure 24:
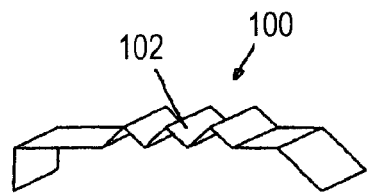

In a further embodiment of the end cap 26, the electrical subassembly 40 is formed with customized components. For example, the lateral terminal pin 46 of the potentiometer 42 may be extended by approximately the length of the contact pin 50, so that it is possible to dispense with the latter. The terminal pin 44 of the potentiometer 42 can be adapted such that the transition to the other element in the circuit takes place smoothly. Further simplification of the construction of the electrical subassembly 40 can be achieved by the helical spring 52 on the one hand being electrically connected to the central terminal pin 44 and on the other hand lying against the plate-shaped end region of the connecting pin 36' in a contact-making manner. This achieves the effect that it is possible to dispense with the litz wire 48. In a further embodiment, a leaf spring 100 according to FIG. 23 or FIG. 24 is used instead of the helical spring 52 and the litz wire 48. When one of these leaf springs 100 is used, the central terminal pin 44 is made very short, for example by a surface-area contact on the terminal side of the potentiometer 42. A contact region of the leaf spring 100 that is angled away at right angles is placed against or connected to this contact in an electrically conducting manner. The opposite end of the leaf spring 100 is angled away at an angle of from 20 to 70 degrees, preferably from 40 to 50 degrees, whereby a spring effect is produced. This end region is brought into contact with the connecting pin 36' in a contact-making manner. The leaf spring 100 shown in FIG. 24 additionally has, arranged between the two contact ends of the leaf spring 100, a bellows-like spring portion 102, which increases the resilient effect of the leaf spring 100 in its longitudinal axis. In a further embodiment, it is likewise possible to dispense with the connecting pin 36', the length of the helical spring 52 then having to be increased and this spring forming the contact element 36 with respect to the energy store and, via the shim, with respect to the potentiometer 42, the electrical conductivity of the spring having to be optimized in this embodiment. In a further configurational variant, the leaf spring may also be extended, so that it forms the contact element. Furthermore, it is also possible to configure the terminal pin 44 of the potentiometer 42 directly as a resilient contact element, so that it is possible to dispense with the spring, the litz wire 48 and the connecting pin 36'.

In a further embodiment, the driver is formed directly on the setting element 72, whereby assembly is likewise simplified. Moreover, the receptable for the driver on the potentiometer 42 may also be customized, in order that they are formed in a more stable manner than a simple slot. The driver or the receptacle on the potentiometer 42 may for example be formed as an internal hexagon, Torx or cross recess or the like. This force transmission should be designed such that it is similarly stable, like the anti-twist locking. Furthermore, in one possible configurational variant, the free end of the driver may directly form the rotatable or linearly displaceable tap 96 of the potentiometer 42, this of course having to be formed from an electrically conducting material. Furthermore, in this case the potentiometer 42 does not have a housing of its own. Moreover, it is generally possible for the potentiometer 42 not to have a housing of its own, since it is installed in such a way that it is protected in the component. This makes it possible for the part-arc 92, and consequently also the tap 96, to be made larger, in particular wider, whereby heat dissipation or the current flow can be improved. The potentiometer 42 must generally be designed in such a way that on the one hand the current flow and on the other hand the heat dissipation can be ensured. That is to say that both the part-arc 92 and the transitions from and to the part-arc, that is to say from the first contact 94 to the part-arc 92 and from the part-arc 92 to the tap 96, must be correspondingly designed.

Instead of the arrangement of the electrical control element 41 in the end cap 26, it may of course also be arranged in the grip body 22. The control element 41 may be mechanically connected for example to a rotatable, manually actuable setting element, in particular a setting wheel. The circumferential surface of the setting wheel may be provided either completely or only partially over the surrounding surface of the grip body 22. An axis of rotation of the setting wheel either lies in the axis of the grip body 22 or is at least approximately at right angles to said axis. The setting wheel may be arranged between the region where the fingers or thumb rests and the end region of the grip body 22 opposite from the head region 14, preferably at the opposite end of the treatment head or care element 16 or in the region where the fingers rest.

Furthermore, the control element 41 may also be connected to a linearly movable, manually actuable setting element 72 instead of the rotatable setting element 72. In this case, a linearly displaceable potentiometer 42 is preferably likewise used. Such potentiometers are represented in FIG. 17 to FIG. 20 and described below. It goes without saying that the linear movement may also be mechanically converted into a circular movement, or a circular movement may be mechanically converted into a linear movement, by means of a mechanism.

Furthermore, the setting element 72 arranged on the grip body 22 may be spanned by a thin membrane of a soft component, whereby a sealed effect is ensured in the region of the setting element 72.

Figure 17:
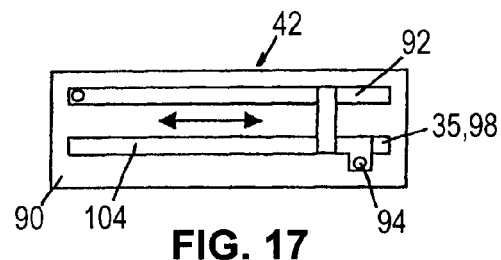
Figure 18:
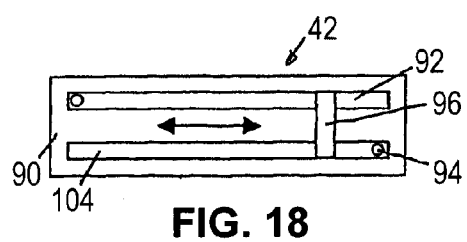

In FIG. 17, an embodiment of a potentiometer 42 with a linearly displaceable tap 96 is shown. A conducting interconnect 104, having a negligible resistance, and an interconnect 92 acting as a resistance path have been applied on a carrier 90. The two interconnects are connected to each other by the linearly displaceable, conducting tap 96. The resistance of the potentiometer 42 is changed by the linear displacement of the tap 96. By analogy with the potentiometer 42 shown in FIG. 13, this potentiometer 42 likewise has a non-conducting end region 98, whereby an on/off switch is likewise formed. A further potentiometer 42 is shown in FIG. 18. This is formed in a way analogous to the potentiometer 42 shown in FIG. 12, but without an on/off switch.

Figure 19:
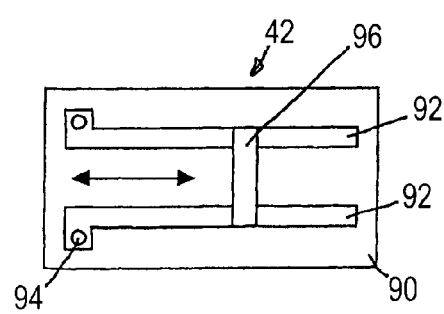
Figure 20:
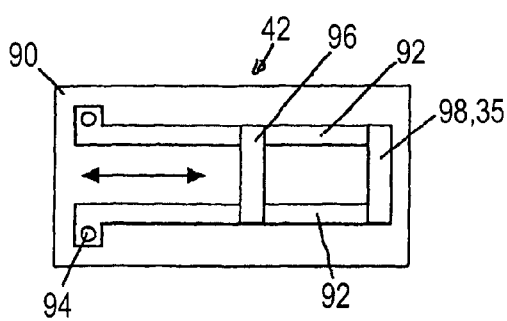

Further potentiometers 42 with linearly displaceable taps are illustrated in FIG. 19 and in FIG. 20. These are distinguished by the fact that both interconnects 92 are formed as resistance paths. This allows the heat produced to be dissipated better. By contrast with the potentiometer 42 shown in FIG. 19, the potentiometer 42 shown in FIG. 20 has an on/off switch that is formed by a non-conducting band 98, onto which the tap 96 can be linearly pushed.

The various constructional possibilities of the linear potentiometer 42 are the same as those of the potentiometer 42 with rotary adjustment. The difference is in the arrangement, linear or indeed rotational.

The direction of movement of the setting element 72 in the case of a linear potentiometer 42 as a control element is preferably parallel to the longitudinal axis of the product, use transversely in relation to the longitudinal axis not being ruled out. The intensity is preferably increased in the direction of the load 33 and reduced in the opposite direction.

Figure 16:
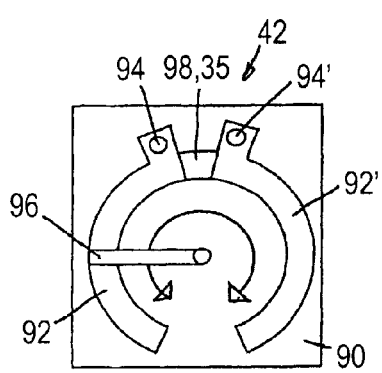

A further embodiment of the personal care device, in particular the toothbrush 12, may have a number of electrical loads 33, for example two. A further load 33 may be a further motor, a heat source, a fluid pump for supplying toothpaste to the head region 14 and so on. In the case where the two electrical loads 33 are used one after the other in time, the potentiometer 42 may be formed as shown in FIG. 16. This potentiometer 42 has a part-arc 92, 92' divided into two, each portion having a first contact 94, 94'. Each of these contacts 94, 94' is electrically connected to one of the two electrical loads 33, so that in each case one or the other can be supplied with current. A part-arc that is preferably smaller in terms of its angle than for only single use in a potentiometer 42 is available for regulating purposes for each of the two loads 33. The two part-arcs may be designed such that each has its own resistance range, specific to the application. An on/off switch is formed by a non-conducting portion between the two part-arcs 92, 92'.

The two separately activatable loads 33 may also be light emitting diodes (LEDs), which can respectively be regulated in a range. Various colors and/or intensities can be generated by the variable supply.

In a further embodiment, two electrical loads 33 may likewise be provided. Each of these loads 33 is connected to a separate potentiometer 42. These may be accommodated in a common housing. Each of these potentiometers 42 can be set by means of a setting element 72 of its own, it also being possible for these to be formed separately from each other or to lie one directly against the other. By means of such an embodiment, it is possible for example for two electric motors to be controlled, one bringing about a rotational movement of a bristle carrier 118 and the other electric motor bringing about a vibration of the bristle carrier. The individual activatability of the two electric motors allows the cleaning performance of the toothbrush 12 to be optimized.

As an alternative to the bristle covering 18 shown in FIG. 1, the treatment region 15 of the toothbrush 12 may have a differently formed bristle covering with additional rubber-elastic elements 110 for massaging and/or for cleaning. Such treatment regions are shown in FIG. 25 to FIG. 33. For the sake of better overall clarity, not all the bristle clusters 18' comprising conventional bristles, for example of polyamide PA or polyester PBT of the bristle covering 18 (see FIG. 1) are shown in some instances, but instead only their receiving holes in the hard component, or rubber-elastic elements 110. The conventional bristles usually have diameters of less than 0.25 mm. The rubber-elastic cleaning elements usually have much greater cross sections.

Figure 25:
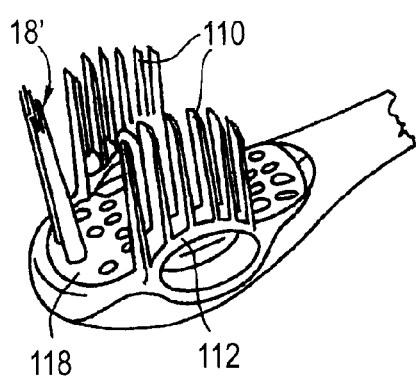
FIGS. 25-33 show different bristle coverings for the toothbrush according to FIG. 1 in a perspective representation or side view.

The treatment region represented in FIG. 25 has a number of rubber-elastic elements 110 on both sides, with respect to the longitudinal axis of the toothbrush 12, to the sides of the bristle covering 18. The rubber-elastic elements 110 are integrally molded to a resilient, ovally formed soft plastic ring 112, which for its part is connected, in particular integrally molded, to the bristle carrier 118 produced from a hard component. The rubber-elastic elements 110 are arranged at least approximately parallel to the bristle clusters 18'. The integral molding of the rubber-elastic elements 110 onto the soft rubber rings 112 and soft mounting thereby achieved has the effect that they respond particularly well to the vibration. The consequently softly mounted rubber-elastic cleaning elements 110 achieve a greater deflection than the conventional bristles 18.

Figure 26:
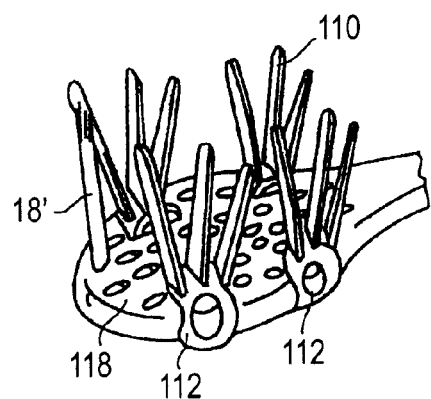

The treatment region represented in FIG. 26 has four soft rubber rings 112, to each of which three rubber-elastic elements 110 are integrally molded. Every two soft plastic rings 112 are arranged on the same side of the bristle covering. The soft rubber rings 112 together with the rubber-elastic elements 110 are preferably integrally molded directly onto the hard component of the bristle carrier 118. The rubber-elastic elements 110 may have the same direction as the bristles or they may be at an angle to them of between 0 and 45 degrees, in which case they preferably extend away radially from the center point of the plastic ring.

The soft plastic rings represented in FIGS. 25 and 26 do not necessarily have to be circular rings. Configuration of the "rings" as oval or as other closed curves is not ruled out. The forming of the soft plastic rings preferably takes place during the injection-molding process in the injection molding tool by means of side slides. The rings 112 and the cleaning elements 110 may also consist of different materials, for example of soft components of different Shore A hardness. In this case, the cleaning elements 110 are preferably produced from softer materials than the rings.

Figure 27:
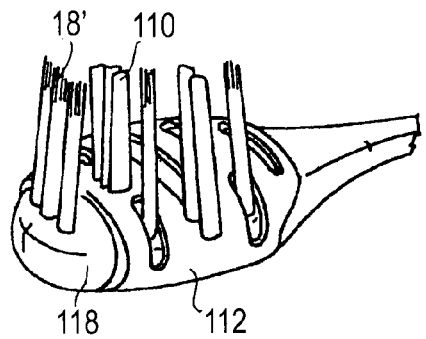
Figure 28:
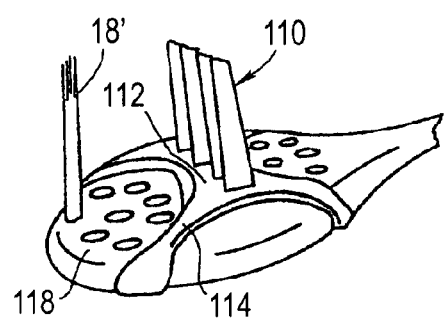

The treatment region represented in FIG. 27 has a soft plastic bridge 112, which spans the bristle carrier 118 transversely in relation to the longitudinal direction of the toothbrush 12. The soft plastic bridge 112 has clearances, through which the bristles 18' anchored in the bristle carrier 118 are led. Integrally formed on the soft plastic bridge 112 are a number of rubber-elastic elements 110. The soft plastic bridge may be integrally molded on at the sides of the toothbrush head or it may be integrally molded on the side of the brush head that is opposite from the bristle zone.

In FIG. 28, once again a soft plastic bridge 112 is shown. The rubber-elastic elements 110 aligned parallel to the bristle clusters 18' are integrally molded on a middle piece, from which four arms 114 protrude, engaging at least partially around the bristle carrier 118 and integrally molded onto it at the sides or on the underside.

In FIGS. 25 to 30, the bridges or annular resilient structures may have clearances through which conventional bristles lead. Moreover, all the structures may include cleaning elements 110 of a soft component, which are integrally molded directly on the bridges or annular structures. The maximum distance between the underside of these resilient structures and the upper side of the brush head is less than 8 mm, preferably less than 5 mm.

Figure 29:
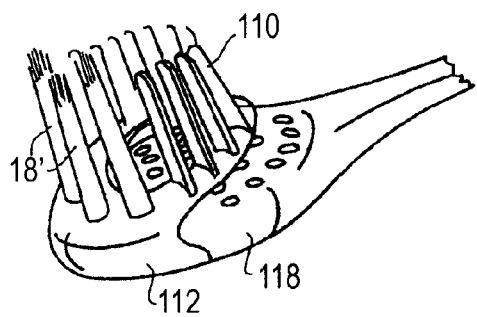
Figure 30:
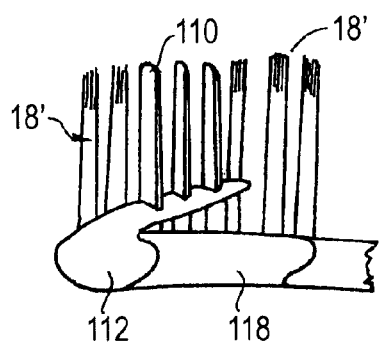

Shown in FIG. 29 and FIG. 30 is a treatment region, the rubber-elastic elements 110 of which are arranged on a soft plastic rocker 112. The latter is integrally formed, preferably molded, on the free end of the bristle carrier 118 in the longitudinal direction of the toothbrush 12. The free portion of the soft plastic rocker 112 on which the rubber-elastic elements 110 are integrally formed is formed in an annular manner. Individual bristle clusters 18' reach through the soft plastic rocker 112 in the hole of the ring and near the region where it is connected to the bristle carrier 112. The soft plastic rocker may also be supported by columns in certain regions (not shown).

Figures 31, 32:
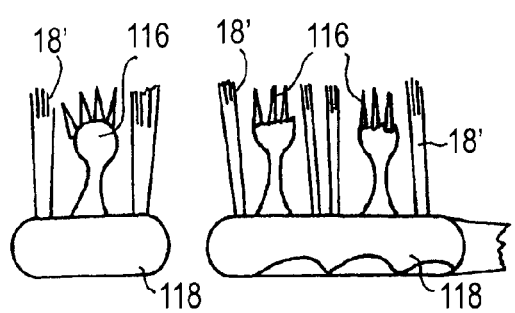

A further embodiment of the treatment region with rubber-elastic elements 110 is shown in FIG. 31 and FIG. 32. The rubber-elastic elements 110 are fastened, preferably integrally molded, directly on the front side of the brush head. The elements 110 have at their free end a ball-like thickening 116, from which finer massaging and cleaning elements extend.

Figure 33:
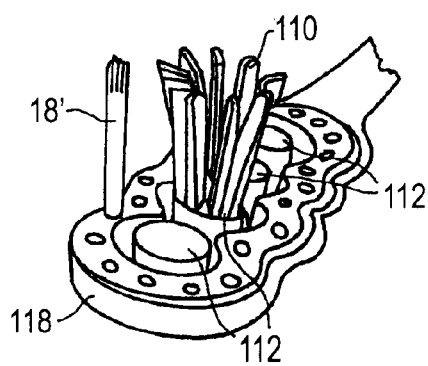

A further exemplary embodiment of a treatment region is shown in FIG. 33. A bristle carrier 118 is formed from a hard component shaped in a shell-like manner, which has a base and a peripheral region protruding from it. The conventional bristle clusters 18' of the bristle covering 18 are anchored in the hard component in the peripheral region of the bristle carrier 118. A number of islands 112 of soft material have been applied, or integrally molded, onto the base, from which islands the rubber-elastic elements 110 protrude. The alignments of the bristle clusters 18' and the rubber-elastic elements 110 are at least approximately the same.

The different coverage of the head region 14 with elements comprising bristles and other soft-elastic massaging and/or cleaning elements has the consequence that elements with different natural frequencies are arranged in the brush head. Of these, the conventional bristles oscillate less than the soft-elastic elements 110, it being attempted by means of regulating the motor speed to bring the soft-elastic elements 110 to natural frequency. In turn, other effects can be achieved if the bristles are attached to the head region 14 by means of the AFT (anchor-free tufting) or IMT (inmold tufting) method.

Figure 2:
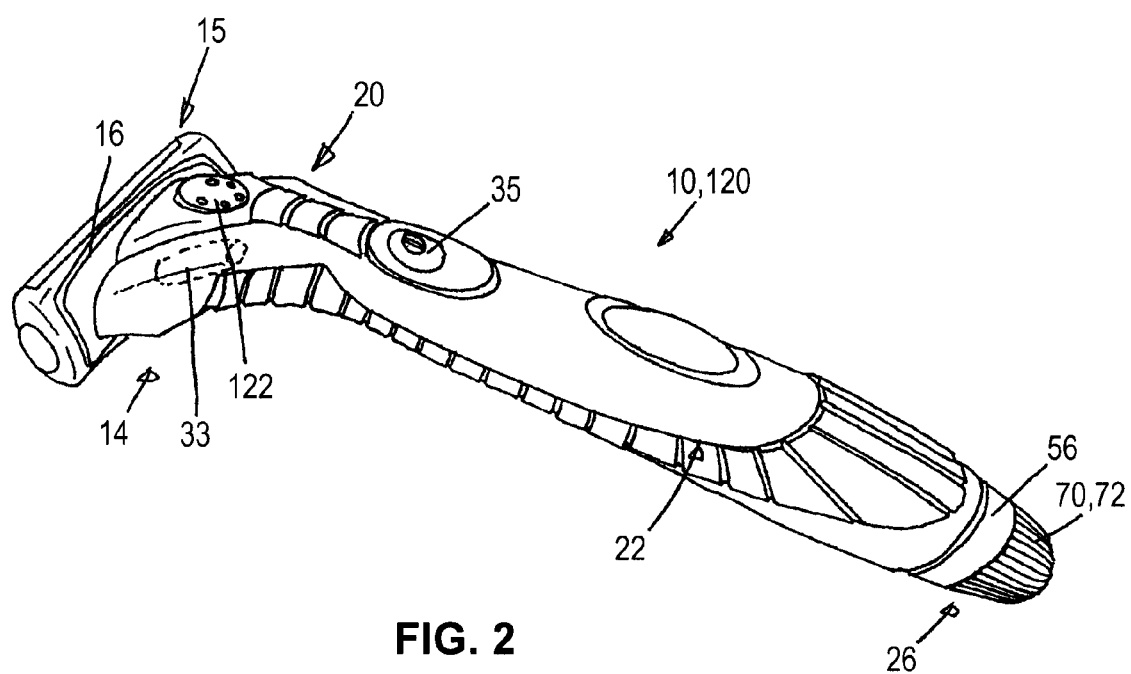
FIG. 2 shows a wet razor according to the invention with the end cap, which contains the control element.

A personal care device 10 formed as a wet razor 120 is shown in FIG. 2. The end cap 26 of this razor 120 is formed largely in the same way as the end cap 26 disclosed in conjunction with FIG. 1, apart from the external design and the dimensions. The grip body 22 of the razor 120 is likewise designed largely in the same way as the grip body 22 of the toothbrush 12 disclosed in conjunction with FIG. 1. The razor 120 has an on/off switch 35, which is formed in a way analogous to that of the toothbrush 112. Integrally formed adjoining the grip body 22 and opposite from the end cap 26 is a neck region 20 of the razor 120. The free end region of the neck region 20 is provided with an exchangeable blade holder, which exposes a blade held in the treatment region 15 by actuation of an exchange button 122. For the construction, operating mode, production and materials used for the end cap 26, you are referred to the above description of the figures concerning the toothbrush 12. Arranged in the neck region 20 is a motor forming an electrical load 33, which is intended for setting the treatment region in vibration. The existing end cap of the razor, disclosed in EP-A-1 563 967, can be exchanged directly for the end cap 26 with a control element that is disclosed in said document, without any adaptations to the product, the razor, being necessary.

For the wet razor 120 with an electrically operated functional element, the functional element may be assigned functions that are analogous to those for the toothbrush 12. For example, light sources, fluid pumps, heat sources, electric and magnetic fields or other electrical loads, such as for example a long hair cutter, may be controlled by the present electric circuit in the end cap 26'.

For the construction, operating mode, composition of the materials and production process of the further elements, in particular the grip body 22, the neck region 20 and the exchangeable blade holder, you are referred to EP-A-1 563 967. This application discloses on the one hand an electrically operated razor that is operated with a storage battery and on the other hand an electrically operated razor that is operated with a battery. The end cap disclosed in EP-A-1 563 967 can be exchanged for the end cap 26 according to the invention.

It goes without saying that the setting element 72, as described in conjunction with the toothbrush 12, may also be arranged on the grip body 22 and be formed in a linearly displaceable or rotatable manner. Further embodiments of the toothbrush 12 can be largely transferred analogously to the razor 120.

The implementation of some further possible embodiments of loads 33 in a wet razor is to be mentioned below by way of example. In the same way as the mascara applicators described below, heating elements 140 for generating heat in an exchangeable blade 142 of the razor 120 may also be fitted for example. These heating elements may be realized in the form of a resistance wire or a resistance heater or small flat resistors, for example SMD resistors (surface mounted device resistors) or chip resistors. These may either be regulated by means of a controller or be designed as self-regulating resistors. The heating elements 140 may be arranged under the blades 142, or before the engagement of the blades 142, in order to heat up the hairs briefly, and/or after the cut, or above the blades, in order to care for the skin after the cut.

Figure 43:
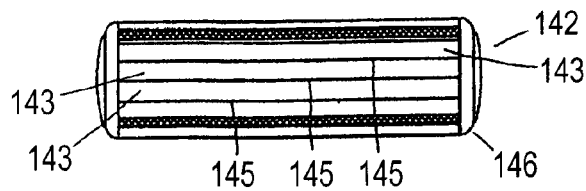
FIG. 43 shows a known exchangeable blade for a wet razor in plan view.
Figure 44:
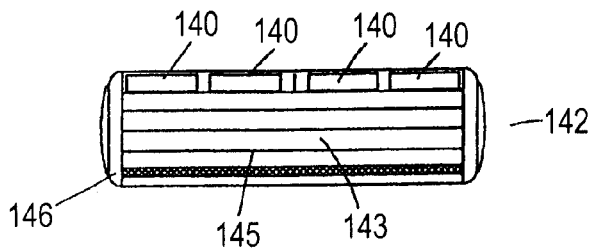
FIGS. 44-45 show exchangeable blades for wet razors in plan views, with heating elements or a heating strip.
Figure 45:
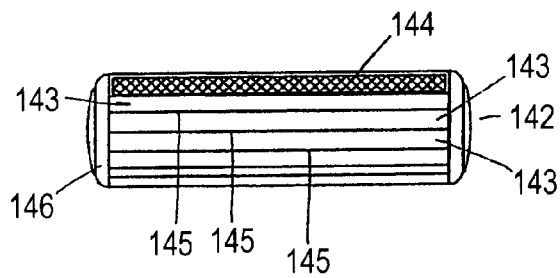
Figure 46:
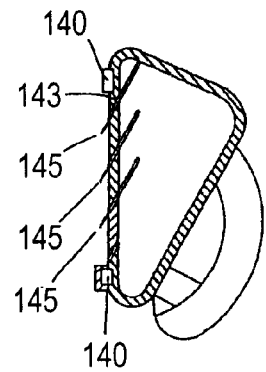
FIG. 46 shows an exchangeable blade according to the invention in a cross section, with heating elements arranged on the frame of the exchangeable blade above and below cutting edges of the blade cutters.

Various blade units are represented in FIGS. 43 to 45. FIG. 43 shows by way of example a standard exchangeable blade 142. FIGS. 44 and 45 show heating elements 140 or heating strips 144 provided above blade cutters 143. The heating elements 140 should be arranged at the same height or slightly below cutting edges 145 of the blade cutters 143 in side view. To anchor the heating elements 140 on the exchangeable blade 142, they may be mounted on a hard plastic component of an exchangeable blade frame 146 and be overmolded with a further plastic component by means of injection molding. For example, a soft plastic component could be used for the overmolding, in particular if, as shown in FIG. 46, the heating element 140 is arranged under the cutting edge 145 of the blade cutters 143, and consequently before the blade engagement, i.e. before the cutting edges 145 of the blade cutters 143 in the direction of movement of the exchangeable blade 142 as intended. The plastic component that is used for the overmolding may also be provided with an active substance or be of such a nature that it wears away during use. The active substance is for example a water-soluble injection-moldable polymer, for example based on polyethylene oxide (Polyox) or PEG (polyethylene glycol). If the heating element 140 is arranged after the engagement of the blade, the heating element 140 may be surrounded or covered by skin-caring agents, which are for example, as already described, integrated directly in the plastic. These skin-caring agents then dissolve at a faster or slower rate according to the temperature that is set, i.e. the exchangeable blade 142 then dispenses more or less agent onto the skin. In particular, the skin-caring agents may be incorporated in water-soluble, thermoplastic materials that can be processed by means of injection molding, with which the heating elements 140 are encapsulated. Alternatively, fats, oils, waxes or other lubricating agents or agents that improve the sliding properties may also be dispensed. By means of the proposed thermal energy, these also dissolve better and the dispensing can be made to correspond to requirements by the individual adjustment of the setting element 72. Moreover, it should be mentioned that, in the case of toothbrushes 12, exchangeable blades 142 and mascara brushes 130, etc., the heating element 140 for generating heat may not only comprise a heating wire/resistance wire or a resistance element but also electrically conducting plastic which has been applied to the desired locations by means of injection molding.

The conducting plastic is then electrically connected to the assigned terminals in a way analogous to resistance wires and heats up correspondingly in the state in which it is flowed through by electric current.

Both single-component and multi-component injection-molding processes may be used for producing regions with electrically conducting plastic, in order at the same time also to produce further parts of the application head (brush head, mascara brush head, changeable blade, etc.) from plastic. Preferably, the electrically conducting plastic bonds with a surrounding plastic or a connection with respect to the other plastics is created by means of positive engagement. The electrical plastic is at least partially surrounded by non-conducting parts, for example of non-conducting plastic.

Figure 47:
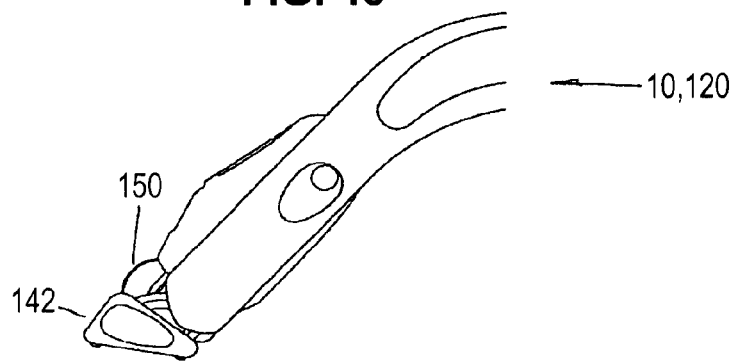
FIG. 47 shows an embodiment of a wet razor according to the invention in side view, with an electrical plug-in connection between the exchangeable blade and a neck region of the wet razor.
Figure 48:
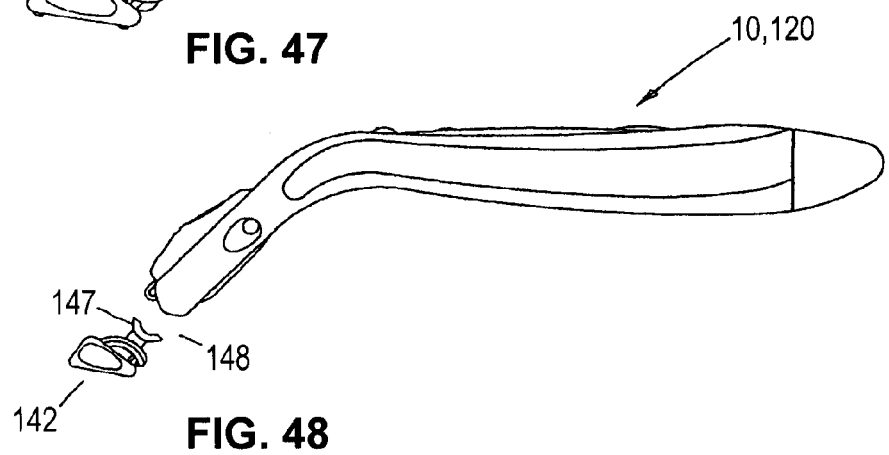
FIG. 48 shows a further embodiment of a wet razor according to the invention in a side view, with movable electrical contacts on a change-over coupling between the exchangeable blade and the neck region.

It goes without saying that the exchangeable blade 142 must be supplied with electrical energy. Here there is the possibility of using moving contacts 147 by means of physical contact (sliding contacts) between the exchangeable blade 142 and the grip of the wet razor or integrating them in a change-over coupling 148, as represented in FIG. 48. In both cases, electrically conducting plastics may also be used instead of electrically conducting wires for the conduction of the electric current. Water and shaving foam make these contacts easily become soiled or susceptible to corrosion. Preferred, however, is an energy transmission by means of a plug-in connection and flexible interconnects or cables, as represented for example in FIG. 47. With this type of energy transmission, the contacts are fixed, i.e., when the exchangeable blade 142 changes its position, the positions of the contacts in relation to one another do not change. It is also possible for the flexible interconnects or cables to additionally provide the exchangeable blade 142 with flexible resilience. This type of energy transmission can also be applied to other loads 33 in the exchangeable blade. The plug-in connection described may be realized on the upper side or the underside of the razor 120.

As a further example, a light source may be accommodated in the exchangeable blade 142 of the wet razor, for example by means of an LED/OLED or a luminescent film/electroluminescent film (EL film). Preferably, for cost reasons, the expensive electrical components are in this case accommodated in the grip body 22 and only the minimally required components are accommodated in the exchangeable blade 142. When an LED is used, the LED is consequently preferably fitted in the handle and a light coupling is set up with respect to the exchangeable blade 142 by means of light-conducting materials, such as for example transparent plastics, light-conducting glass fibers, etc., in order to conduct the light to the exchangeable blade 142 at the intended location. The use of a light guide for the transmission of the light into the exchangeable blade 142 may take place in a way analogous to the electrical transmission in FIG. 47. If the light on the exchangeable blade 142 is to be generated by means of a luminescent film, the energy is again transmitted to the exchangeable blade 142 by means of electric current in a way according to the previously discussed example of the heating elements 140. In the case of the luminescent film, the expensive electrical components for feeding the luminescent film are likewise accommodated in the handle of the wet razor 120. By analogy with the heating elements 140, the illuminating means may again be placed on a strip under the lowermost blade cutter 143 before the blade engagement, i.e. before the cutting edges 145 of the blade cutters 143 in the direction of movement of the exchangeable blade 142 as intended, or on a strip above the uppermost blade cutter 143, that is to say after the blade engagement, i.e. after the cutting edges 145 of the blade cutters 143 in the direction of movement of the exchangeable blade 142 as intended. The light emission at the exchangeable blade may for example assume an antibacterial function by means of blue light or initiate a reaction with the shaving foam that is used. The current conduction for the illuminating means may, in particular in the case of relatively small currents, once again take place by means of electrically conducting plastics already mentioned above.

Further electrically operated personal care devices 10 according to the invention that are formed as mascara applicators 124 are disclosed in FIG. 34-FIG. 39. We are only concerned here with the application devices, not the mascara, which is preferably formed in a conventional manner as known on the market.

Figure 34:
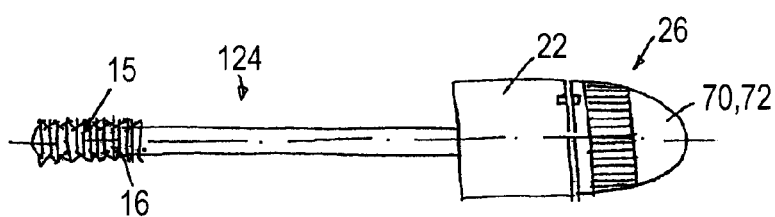
FIGS. 34-37 show various embodiments of an electrically operated mascara applicator.
Figure 35:
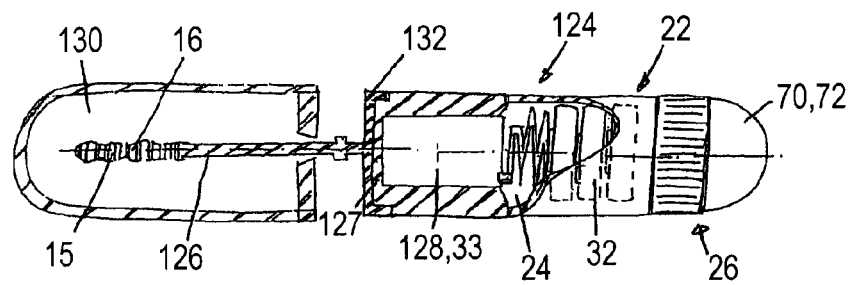

FIGS. 34 and 35 show two embodiments of a mascara applicator 124. In this configurational example, the mascara applicator 124 has a circular-cylindrical grip body 22 with an end cap 26 arranged on it on one side and a mascara brush 126 arranged on it on the other side, said brush forming the care element 16 of the mascara applicator. Furthermore, the grip body 22 has an interior space 24 (see FIG. 35), which is closed by the end cap 26. The end cap 26 with the manually actuable setting element 72, by means of which the control element contained in the end cap 26 can be actuated, is largely the same as the end cap 26 of the toothbrush 12 (see FIG. 1 as well as FIGS. 3 to 11). For the assembly, configuration and materials used, you are referred to the above description in conjunction with the toothbrush 12. The end cap according to the invention or the control element according to the invention may be used both in the case of vibrating application of a mascara brush and in the case of all other applications of a mascara brush that are discussed further below.

Instead of the bayonet closure disclosed in conjunction with the toothbrush 12, a latching connection may also be used between the end cap 26 and the grip body 22. This latching connection is formed in a way analogous to the latching connection between the shell part 56 (see FIG. 6) and the core part 54.

An electrical load 33 that is shown in FIG. 35 and is formed as a vibration element (motor with unbalance—shown in FIG. 39) 128 is fitted in the interior space 24 and lies firmly against an end wall 127 that delimits the interior space 24 and is opposite from the end cap 26. Arranged opposite the vibration element 128, on the end wall 127, is a brush holder 132, which is produced integrally with the mascara brush 126. The mascara brush 126, which has the treatment region 15 at its free end region, is consequently coupled with the vibration element 128, so that the vibrations are transmitted to the treatment region 15.

Also arranged in the interior space 24 is an energy store 22, which is electrically connected to the vibration element 128 via the electrical control element arranged in the end cap 26. Consequently, the intensity of the vibration can be steplessly set by means of the setting element arranged in the end cap 26, whereby the application of mascara to the eyelashes is improved, since the eyelashes are separated from one another by the vibration of the mascara brush. The vibrations also make it possible for the mascara to be applied uniformly.

The frequency of the vibration lies below 300 Hz, preferably below 200 Hz, with an only small deflection of preferably less than 1 mm in the free end region of the treatment region 15 when the device is held in the hand in the normal way. Vibrations that are too strong may make the mascara spatter or individual lashes stick together.

A control element with an on/off switch that is formed as a potentiometer 42 and preferably has the "off" position thereafter toward the region of greatest resistance (see FIG. 14) is fitted in the end cap 26. Alternatively, a microswitch (with a fixed on/off position) with a base area smaller than 8 mm times 8 mm may be used. Another configurational variant provides that the switch is activated when the mascara container 130 is removed. This ensures that the device only operates when the mascara brush is exposed. Conversely, it is advisable that the current flow is necessarily deactivated when the mascara container is fitted on.

Used with preference as the vibration element 128 is an electric motor with a power consumption of less than 0.5 watts. A vibrational force generated by the vibration element 128 preferably lies below 1.3 G, in particular below 1 G, with G denoting gravitational force. In cases of greater vibrational forces, drops of mascara could spray away from the mascara brush. To generate this vibrational force, an eccentric of the vibration motor preferably has a length below 5 mm and a weight of below 1.5 g, preferably of below 1 g. The weight refers to the proportion by volume of the eccentric that produces an eccentric effect. Furthermore, the contact between the electrical load 33 and the energy store 32 is established by means of a spring, whereby good contact is ensured. The circuit diagram of the electric circuit contained in the grip body 22 and the end cap 26 is shown in FIG. 20 and corresponds to that of the toothbrush 12.

The mascara applicator 124 has from the free end of the mascara brush 126 to the free end of the end cap 26 a length of preferably 70 mm to 150 mm, preferably between 85 mm and 135 mm. The length of the grip body 22 with the end cap 26 arranged on it lies with preference between 20 mm and 70 mm, preferably between 35 mm and 55 mm. The length of the mascara brush 126 lies with preference between 30 mm and 100 mm, preferably between 40 mm and 85 mm, of which the actual brush part lies in the range between 10 mm and 40 mm, preferably 20 mm and 30 mm. The energy store 32 built into the grip body 22 preferably has a weight of below 15 g and a length of below 50 mm. This mass does not adversely influence the ergonomics and exact guidance of the mascara brush. For this reason, it is appropriate to use a battery of the type AAA, with 1.5 V, or—as shown in FIG. 35—a number of button cells, which is preferred.

As shown in FIG. 35, the mascara brush 126 can be inserted into a mascara container 130. The mascara brush 126 is inserted in the mascara container 130 through a round opening. The mascara brush 126 has near the grip body 22 a thickening, which interacts with the opening in the mascara container 130 to guard against escape of the mascara from the mascara container 130 in the state in which the mascara brush 126 has been inserted completely into the mascara container 130.

Figure 36:
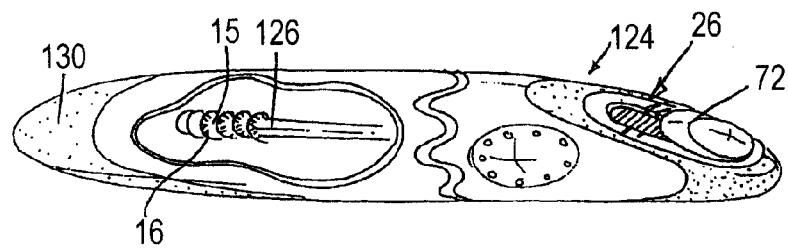

An alternative configuration of the mascara applicator 124, which has a linearly displaceable setting element 72, is shown in FIG. 36. Consequently, a potentiometer 42 with a linearly displaceable tap 96, for example one according to FIG. 17 or FIG. 20, is preferably used.

Figure 37:
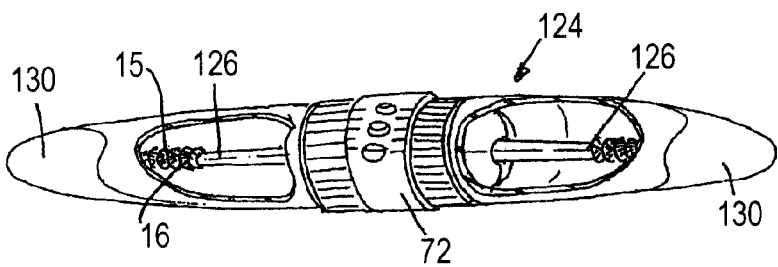

In FIG. 37, a mascara applicator 124 with two mascara-filled mascara containers 130 that are separate from each other is shown. On the one hand, the grip body 22 arranged between the two mascara brushes 126 serves for fastening the mascara containers 130 when they are not in use and on the other hand the energy store, the load and the control element for the electrical application are accommodated in the grip body 22. The load is formed as a vibration element and, as a result of the arrangement between the two mascara brushes 126, can be used to generate vibrations for both mascara brushes 126. The control of the application takes place with the setting element 72, which is realized on the surface of the grip by a peripheral ring. The control of the application can be performed by turning the ring or the setting element 72, allowing not only the individual variation of the intensity of the vibration but also the switching on and off of the application. Alternatively, a separate switch—either manually actuated or forcibly controlled by the removal or fitting of the mascara container 126—may also be used in the case of this variant. The arrangement of a ring on the grip body as a setting element may also be provided in the case of the other personal care products according to the invention. Preferably, the ring is likewise sealed toward the inside, in order that water cannot get into the device.

Figure 38:
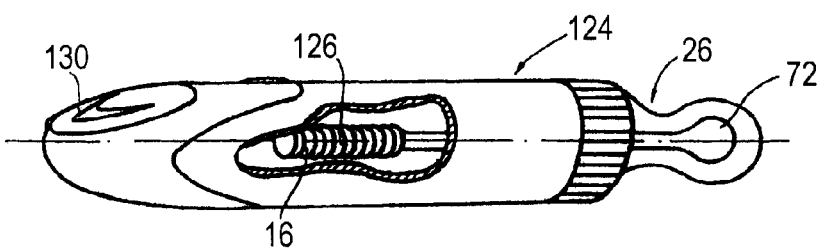

A further embodiment of a mascara applicator 124 is shown in FIG. 38. The end cap 26 of this applicator 124 is provided with a setting element 72 that is linearly displaceable, in the axial direction of the mascara brush 126. This setting element is formed as a rod and is mechanically connected to the control element. The free end region has a ball-like thickening. A potentiometer 42 with a linearly displaceable tap 96, as shown in FIG. 17 to FIG. 20, is preferably used as the control element. The setting element 72 is coated with a stretchable soft plastic, which is elastically deformable in the region of the movement of the setting element 72.

Figure 39:
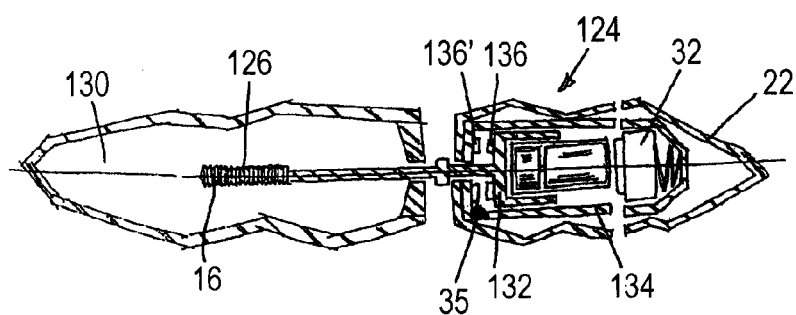

A further embodiment of the grip body 22 is shown in FIG. 39. Arranged in an interior space 24 of the grip body 22 is a cup-shaped brush holder 132, from the cup base of which, on the side opposite from the cup opening, the mascara brush 126 extends away at right angles to the base. Pressed into the cup is a vibration element 128, which has an electric motor and an eccentric. The vibration element 128 has already been described in conjunction with FIG. 35.

The mascara brush holder 132 with the vibration element 128 is arranged in a substantially cylindrical housing 134 and is displaceable with respect to the latter in the direction of the longitudinal axis of the mascara brush 126. Likewise arranged inside the housing 134 is the energy store 32, which is brought to bear against the vibration element 128 by means of a spring.

Also formed on the brush holder 132, on the side of the mascara brush 126, are contact elements 136 and also formed on the housing 134 are counter contact elements 136' interacting with the contact elements 136. Together with the counter contact elements 136', the contact elements 136 form an electrical switch 35. The switch 35 is closed by the contact being closed when the mascara brush 126 is withdrawn from the mascara container 130, as a result of displacement of the brush holder 132 with respect to the housing 134. The brush is thereby displaced with respect to the grip body 22 and the housing 134 by friction, whereby the contact elements 136 are brought to bear against the counter contact elements 136' in an electrically conducting manner. As soon as the mascara brush 126 is inserted into the mascara container 132 again, the brush holder 132 is displaced in the opposite direction by mechanical friction, whereby the electrical contact between the contact elements 136 and the counter contact elements 136' is opened and, as a result, the switch 35 is likewise opened. An electrical control element that can be set from the outside for continuously changing the energy flow between the energy store and the vibration element may also be inserted in the electric circuit, but is not shown in FIG. 35. Such a circuit is shown in conjunction with the toothbrush in FIG. 21 and is explained in the previous explanations concerning the mascara applicators.

As in the case of the vibrating toothbrush 12, it is proposed to cover the treatment region 16 or the treatment head of the mascara brush 126 with various types of bristles (not represented). This achieves the effect that the different types of bristles deflect to a greater or lesser degree. The bristles deflecting to a greater degree provide the separation of lashes that are stuck together and the bristles deflecting to a lesser degree provide the application of the mascara. This can be achieved by means of different diameters, different lengths, different cross sections or different materials of the different types of bristles. With respect to the different materials, in a configurational variant as in the case of the toothbrush 12, a combination of conventional, cylindrical bristles of polyamide PA or polyester PBT with rubber-elastic bristles of soft material, preferably thermoplastic elastomer TPE, can achieve the best effect. Furthermore, bristles pointed in the form of needles may be used in the bristle covering 18.

In a further embodiment of the mascara applicator 124, the mascara brush 126 is not set in vibration but is statically charged. Alternatively, a magnetic and/or electric field could be generated in the region of the bristles of the mascara brush 126. A further embodiment provides for heat to be generated in the region of the bristle-carrying care element. This can be achieved with a resistance wire, preferably with a twisted-in wire designed as a resistance wire, to which the bristles are fixed. The temperature is regulated with the control element and reaches a maximum temperature of 80° C., but preferably a temperature range of 30° C.-60° C. However, it is not only possible for heat introduction to take place directly in the treatment region 16 but also possible for heat input to be produced on the mascara container 130. In this way the effect can be achieved for example that the mascara is heated before application, and so changes its properties or its state of aggregation or its viscosity (hard or viscous in the cold state, liquid in the warm state). The input of heat can in this way take place for example by means of a resistance wire in the mascara in the mascara container 130, by means of sheet-like resistance plates in the mascara in the mascara container 130, by means of such elements on the wall of the mascara container or by means of other heat-transferring elements in the mascara container 130 or on the wall of the latter. The control element is in this case provided on the mascara container 130 instead of on the applicator; the supply of heat to the mascara can be varied.

Apart from regulating the vibration by means of the control element, rotary and translatory movements of the mascara brush 126 may also be controlled. The regulating of the rotary movement allows variation of the rotational speed and/or direction of rotation of the mascara brush 126. In this case, the mascara brush 126 rotates about the longitudinal axis of the mascara applicator 124. Of course, reversing rotational movements, i.e. pivoting movements, of the mascara applicator 124 are also possible. Translational movements of the mascara brush 126 take place in the direction of the longitudinal axis of the mascara applicator 124. It goes without saying that these are also reversing translational movements. The regulating may allow possibilities such as for example the adaptation of the frequency and/or the amplitude of the movement back and forth. With reversing movements of the mascara applicator 124, preferably frequencies of from 50 Hz to 300 Hz, preferably 150 Hz to 250 Hz, are generated. Preferably relatively high frequencies with small amplitudes/angles are provided, in order to obtain a distribution of the mascara that is as good as possible.

As a further exemplary embodiment, a light guide which is fed by a light source in the holding grip may be brought into the region of the care element. This can be achieved by means of a transparent plastic rod or plastic wire which carries the care element or the bristles. The aforementioned resistance wire or light guide may also be firmly clamped between the twisted-in wire during the twisting-in operation. This would make uniform light distribution and heat distribution possible.

By means of one of the exemplary embodiments presented above, together with a corresponding mascara, the amount of mascara that is applied to the lashes can be controlled.

It goes without saying that the intensity of the fields, the light or the temperature can be set by means of a control element as described above.

It goes without saying that the use of an electrical control element for continuously changing the energy flow between the energy store and the load in personal care devices is not only restricted to the exemplary embodiments described above.

For example, light sources, heat sources, magnetic fields and electric fields can also be controlled. It is likewise conceivable to control the volume of a loudspeaker that is built into the personal care device. Furthermore, it is also quite possible for a number of functions to be realized, by using a corresponding potentiometer 42 (as described).

Furthermore, personal care devices, in particular applicators for cosmetic products, applicators for decorative cosmetics and body lotions, such as for example lipsticks, nail varnish and powder brushes, can generally be equipped with an electrical load and an electrical control element that is intended for controlling this load and can be set from the outside. Vibrating or reversing (pivoting, moving back and forth) applicators have the advantage that the medium to be applied is distributed better on a surface and/or penetrates better into pores of the surface. As a result, lasting fixing of the medium on the surface is ensured. The same design data as for the mascara applicator apply to such applicators.

It goes without saying that the configurational variants shown in this document are given by way of example and the individual distinctive features and elements of these configurational variants can be combined or interchanged with other configurational variants without departing from the scope of this invention. In particular, the various loads 33 may be used as combinations or individually on the various devices discussed. It is of course also possible to use the presented devices with the possible loads 33 without an electrical control element. The control element merely serves the purpose of adjusting the loads 33 to the individual requirements of the individual users.

The invention claimed is:

1. An electrically operated personal care device comprising:
    a care element,
    a grip body having an interior space,
    an electrical energy store arranged in the interior space, and
    an electrical load, which is connected to the energy store via a control device having a control element for changing energy flow between the electrical load and the energy store, the control element being set from outside by a setting element, wherein:
    a maximum voltage drop across the control element is limited so functioning of the electrical load as intended is ensured when there is an energy flow with any setting of the control element,
    the control element and the setting element are arranged in a removable end cap, by means of which the interior space is closed, and
    the end cap has two electrical contact elements, which are separate from each other and electrically connected to the control element, and, when the interior space is closed, one of the contact elements is electrically connected to a counter-contact on the grip body and the other of the contact elements is electrically connected to a contact of the energy store.

2. The personal care device as claimed in claim 1, wherein the control element is a mechanically adjustable, electrical resistor, the resistance value of which is defined by the length of the path covered by the current in the resistor.

3. The personal care device as claimed in claim 2, wherein the electrical resistor is formed by a carbon compound, a Ceramed or cermet, from a wound resistance wire or from a conductive plastic.

4. The personal care device as claimed in claim 2, wherein the electrical resistor is a potentiometer.

5. The personal care device as claimed in claim 1, wherein the control device has an on/off switch, which is connected in series with the control element.

6. The personal care device as claimed in claim 5, wherein the on/off switch is integrated in a component of the setting element.

7. The personal care device as claimed in claim 1, wherein the care element is driven by the electrical load.

8. The personal care device as claimed in claim 1, wherein the care element is set in vibration by the electrical load and an intensity of the vibration is set by the control element.

9. The personal care device as claimed in claim 1, wherein the electrical load is an electric motor with an oscillating armature or an oscillating element.

10. The personal care device as claimed in claim 1, wherein the electrical load generates light, sound, heat, an electric field and/or a magnetic field in the care element when energy is supplied.

11. The personal care device as claimed in, claim 1, wherein the control element simultaneously controls a number of electrical loads which can accept different levels of power.

12. The personal care device as claimed in, claim 1, wherein the control element has a resistance of less than or equal to 10Ω when the electrical load is at maximum power.

13. The personal care device as claimed in claim 12, wherein the resistance is less than 1Ω when the electrical load is at maximum power.

14. The personal care device as claimed in claim 1 wherein the control element has a resistance of from 1Ω to 1 MΩ.

15. The personal care device as claimed in claim 14, wherein the resistance is from 1Ω to 50Ω.

16. The personal care device as claimed in claim 1, wherein the control device has a maximum resistance that ensures a minimal starting current or a minimal starting voltage of the electrical load even in the case of a partially discharged energy store.

17. The personal care device as claimed in claim 1, wherein a current intensity of from 0.01 A to 4 A can be set by the control element.

18. The personal care device as claimed in claim 17, wherein the current intensity is from 0.05 A to 1 A.

19. The personal care device as claimed in claim 1 wherein the control element has a weight of less than 10 g and a volume, without projecting contacts, of less than 10,000 $mm^3$.

20. The personal care device as claimed in claim 19, wherein the control element has a weight of less than 2 g.

21. The personal care device as claimed in claim 19, wherein the control element has a volume of less than 500 $mm^3$.

22. The personal care device as claimed in claim 1, wherein the control element and the setting element are rotatably formed, and in that the setting element can be rotated in an angle range of 0° to 350°.

23. The personal care device as claimed in claim 22, wherein the angle range is 0° to 270°.

24. The personal care device as claimed in claim 23, wherein the angle range is 0° to 150°.

25. The personal care device as claimed in claim 1, wherein a torque required for actuating the setting element is less than a torque that is required for releasing the mounted end cap.

26. The personal care device as claimed in claim 1, wherein the control element is kept rotationally fixed with respect to the end cap by an anti-twist locking element.

27. The personal care device as claimed in claim 1, wherein the care element is covered with different types of bristle, which differ in length, cross section and/or the nature of their material, and in that states in which the different types of bristle oscillate/deflect differently can be achieved by the setting of the control element.

28. The personal care device as claimed in claim 1, wherein the personal care device is a toothbrush, the care element being provided with a covering of bristles and arranged on a head region of the toothbrush that is connected to the grip body via a neck region, and the electrical load being arranged in the neck region or head region.

29. The personal care device as claimed in claim 1, wherein the personal care device is a razor, the care element being provided with a razor blade and arranged on a head region of the razor, and the electrical load being arranged in or alongside the head region.

30. The personal care device as claimed in claim 29, wherein the razor is a wet razor.

31. The personal care device as claimed in claim 1, wherein the personal care device is a mascara applicator, the care element being provided with a covering of bristles and connected to the grip body via a brush holder, and the electrical load being arranged in the grip body.

32. The personal care device as claimed in claim 1, wherein an on/off switch is arranged in the grip body.

* * * * *